United States Patent
Oxburgh et al.

(10) Patent No.: US 9,752,115 B2
(45) Date of Patent: Sep. 5, 2017

(54) CULTURE CONDITIONS FOR EXPANSION OF NEPHRON PROGENITOR CELLS

(71) Applicant: Maine Medical Center Research Institute, Scarborough, ME (US)

(72) Inventors: Leif Oxburgh, South Portland, ME (US); Aaron Brown, Scarborough, ME (US)

(73) Assignee: Maine Medical Center Research Institute, Scarborough, ME (US)

( * ) Notice: Subject to any disclaimer, the term of this patent is extended or adjusted under 35 U.S.C. 154(b) by 0 days.

(21) Appl. No.: 14/632,454

(22) Filed: Feb. 26, 2015

(65) Prior Publication Data
US 2015/0275168 A1 Oct. 1, 2015

Related U.S. Application Data

(60) Provisional application No. 61/944,982, filed on Feb. 26, 2014.

(51) Int. Cl.
*C12N 5/00* (2006.01)
*C12N 5/071* (2010.01)

(52) U.S. Cl.
CPC ......... *C12N 5/0018* (2013.01); *C12N 5/0686* (2013.01); *C12N 5/0687* (2013.01); *C12N 2501/105* (2013.01); *C12N 2501/119* (2013.01); *C12N 2501/155* (2013.01); *C12N 2501/415* (2013.01); *C12N 2501/727* (2013.01); *C12N 2501/91* (2013.01); *C12N 2501/999* (2013.01)

(58) Field of Classification Search
CPC .. C12N 5/0018; C12N 5/0687; C12N 5/0686; C12N 2501/91; C12N 2501/105; C12N 2501/415; C12N 2501/119; C12N 2501/999; C12N 2501/155
See application file for complete search history.

(56) References Cited

PUBLICATIONS

Barak et al., Dev Cell. Jun. 12, 2012;22(6)1191-207.*
Takasato et al., Nat Cell Biol. Jan. 2014;16(1):118-126.*
Brown et al., Proc Natl Acad Sci U S A. Mar. 19, 2013;110(12): 4640-4645.*
Araoka et al., PLoS One. Jan. 15, 2014;9(1):e84881.*

* cited by examiner

*Primary Examiner* — Daniel C Gamett
(74) *Attorney, Agent, or Firm* — Mintz Levin Cohn Ferris Glovsky and Popeo, P.C.; David G. Conlin

(57) ABSTRACT

The present invention relates to compositions and methods associated with cocktails of growth factors and small molecules that target specific cell signaling pathways, the cocktails having been formulated to allow/promote the expansion of progenitor cells (e.g., nephron progenitor cells) within a defined culture system.

22 Claims, 34 Drawing Sheets

FIG. 2

Expansion recipe:

Medium – APEL (defined) or DMEM/F12+KOSR
ECM - Matrigel or Gelatin

Factors
FGF9 (200ng/ml)
ROCKi (10uM)
BMP7(30ng/ml)
BMP4( 30ng/ml) – ES cell derivation
LDN (75nM)
CHIR (1uM - low)
IGF1 (20ng/ml)
IGF2 (2ng/ml)

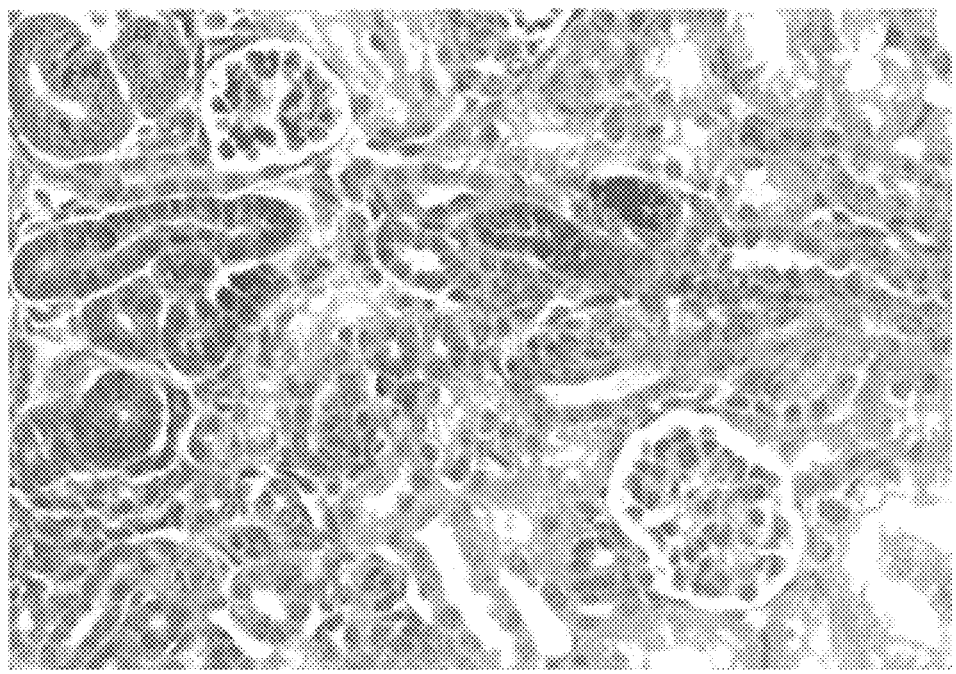
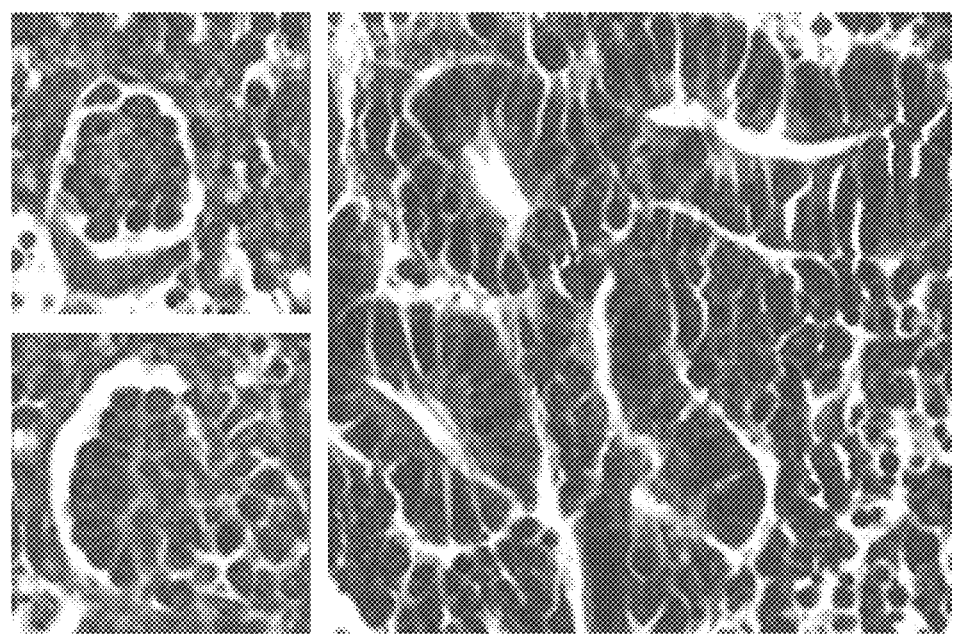
FIG. 5

*Cited1-creERT2-EGFP*

Cited1-creERT2-EGFP (P2)    Six2-creEGFP (P3)

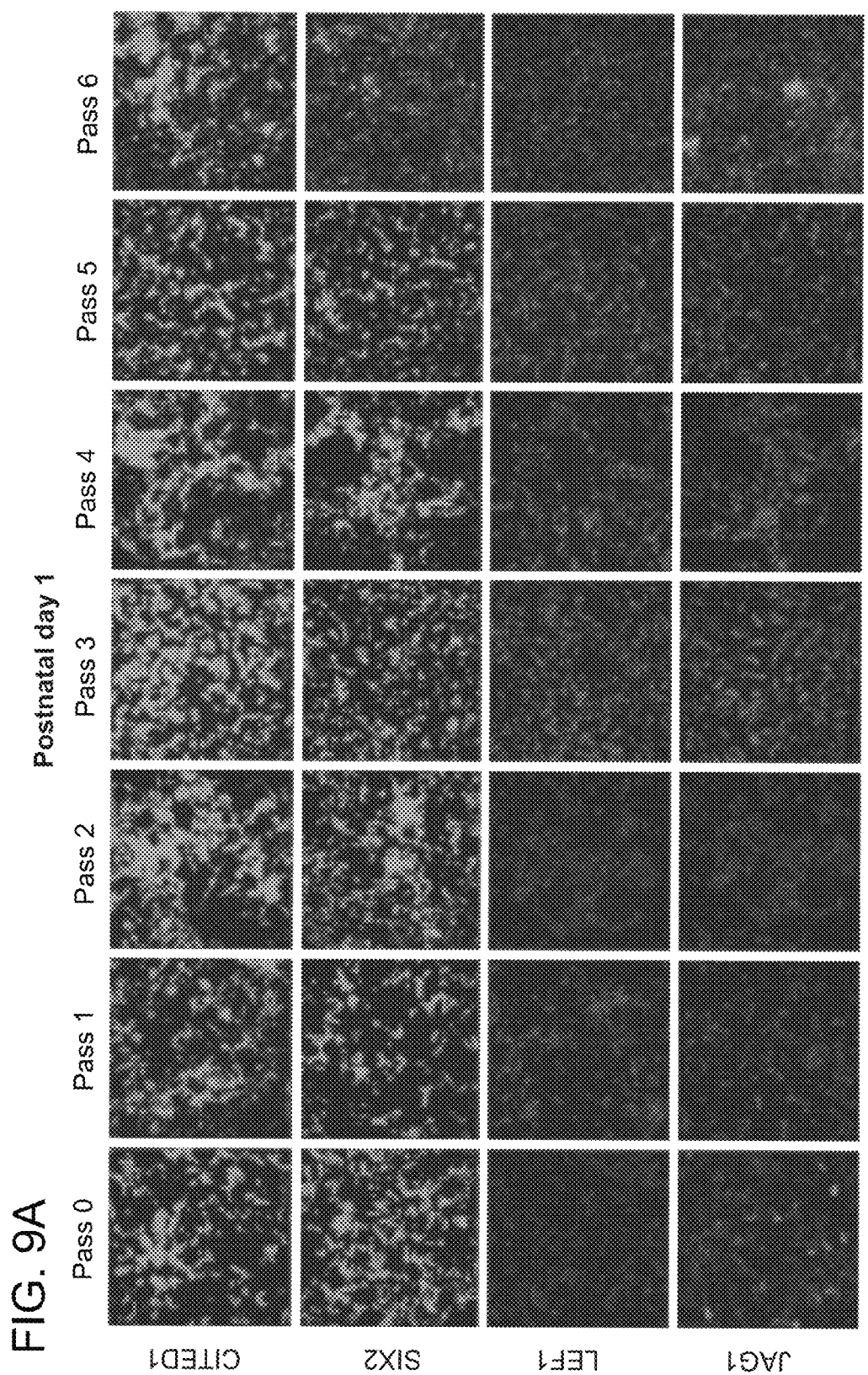

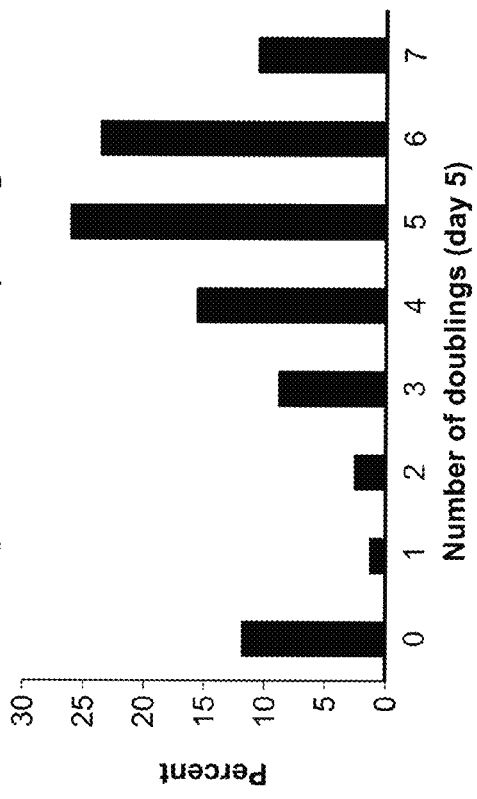
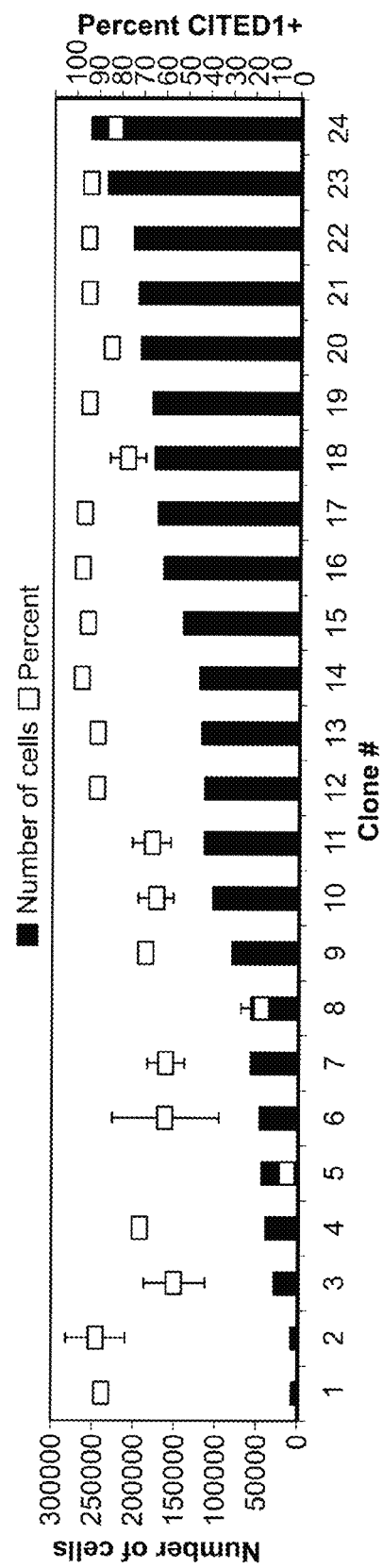
FIG. 11C
FIG. 11D

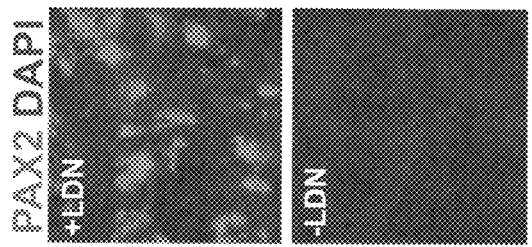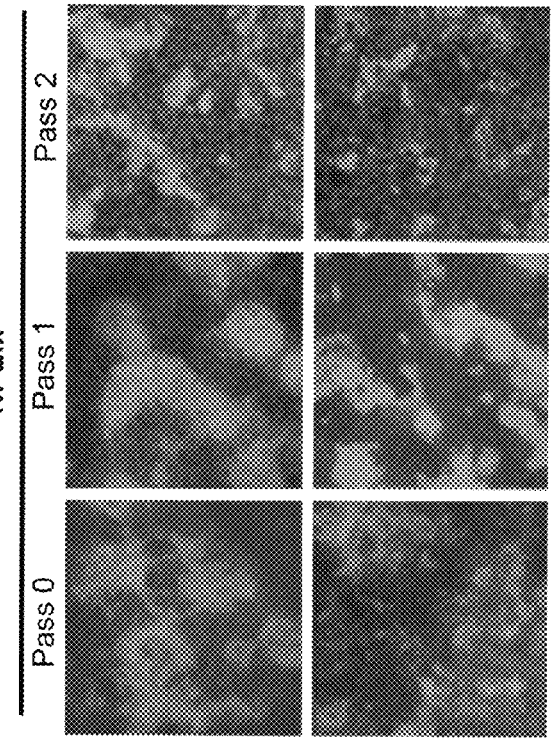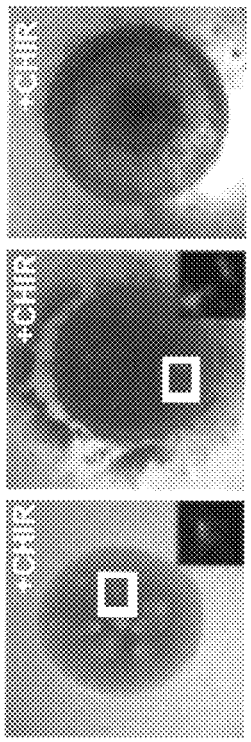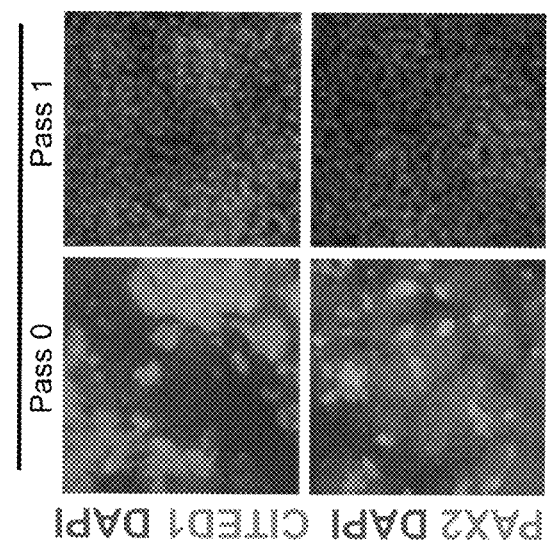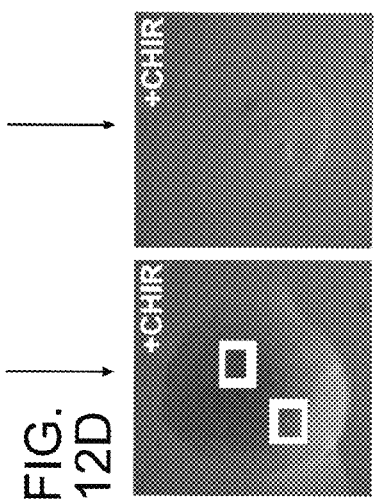

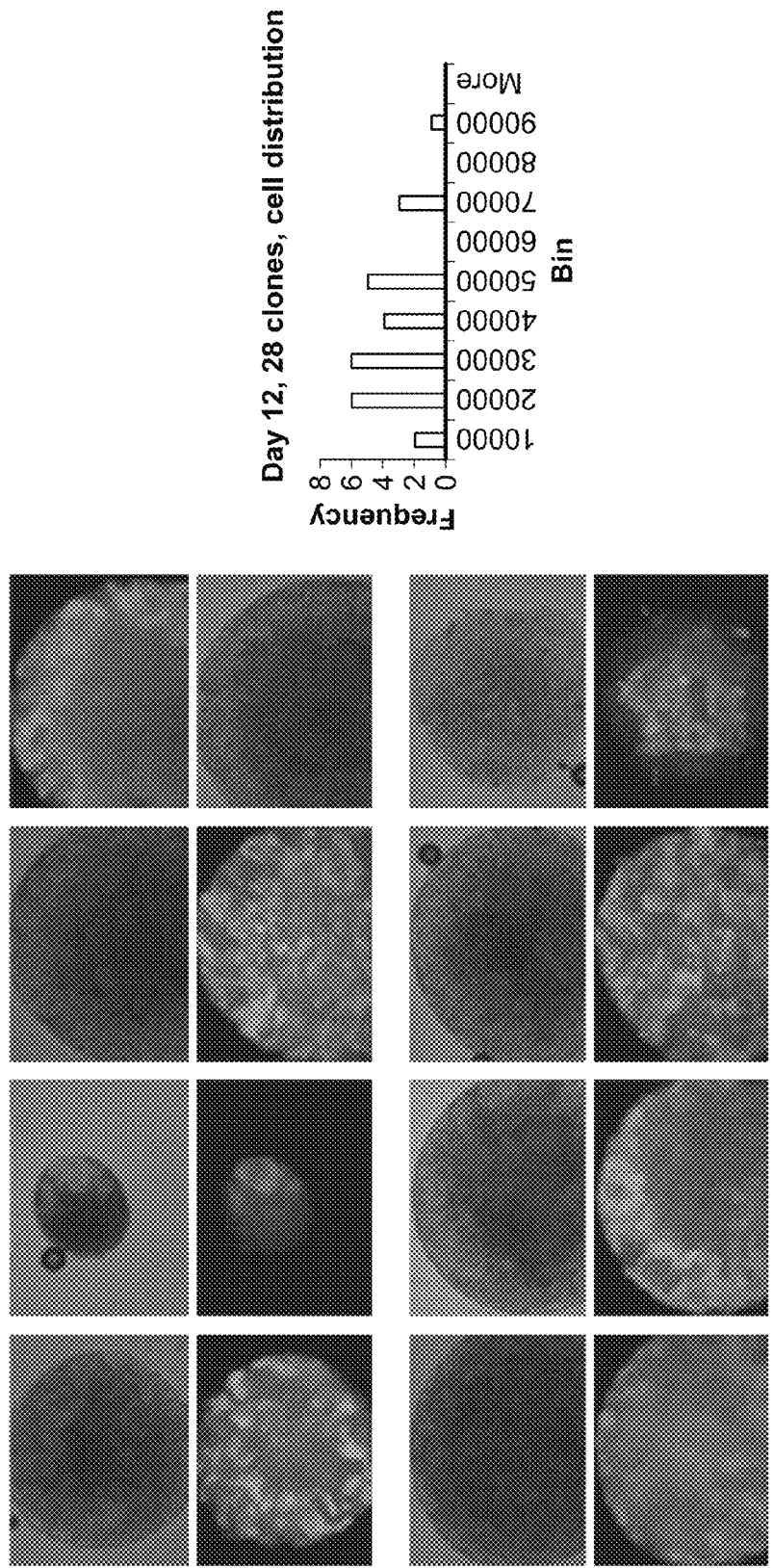

Day 11, pass within well, Day 13 count (average was 58,267) and this ag 128,800 = 18 hr doubling Pass 0

Pass 2

CULTURE CONDITIONS FOR EXPANSION OF NEPHRON PROGENITOR CELLS

CROSS-REFERENCE TO RELATED APPLICATIONS

The present application claims priority to, and the benefit under 35 U.S.C. §119(e) of, U.S. provisional patent application No. 61/944,982, filed Feb. 26, 2014, entitled, "Culture Conditions for Expansion of Nephron Progenitor Cells". The entire contents of the aforementioned patent application are incorporated herein by this reference.

STATEMENT REGARDING FEDERALLY SPONSORED RESEARCH OR DEVELOPMENT

Research supporting this application was carried out in part under funding from the United States Government, Grant/Contract Number W81XWH-12-1-0468. The government of the United States has rights in the inventions.

FIELD OF THE INVENTION

The invention relates to development of a chemically defined medium for long term culture and expansion of nephron progenitors for the purposes of studying kidney organogenesris and developing therapies to treat kidney disease.

BACKGROUND OF THE INVENTION

The nephron is the filtering unit of the kidney and is essential for regulating blood urea concentration and limiting water and electrolyte loss. Nephron formation is limited to the fetal period in humans and continues to postnatal day 4 (P4) in rodents. After this period of kidney development, new nephrons can no longer be formed. Since the mature kidney lacks an identifiable population of stem cells and has a limited capacity to repair itself after injury, its long-term function relies on nephron over-capacity, which is determined during the fetal/postnatal period (Humphreys et al., 2008; Little and Bertram, 2009). Urea excretion can be augmented by dialysis, but transplantation is eventually required for patients with severe organ function impairment. End-stage renal disease affects approximately 500,000 individuals in the United States and organ availability does not match demand (Abdel-Kader et al., 2009). Technology for ex vivo nephrogenesis would enable therapeutic replacement of damaged kidney tissue, and provide human tissue with which to study kidney development and the origins of kidney disease. Rapid advances in reprogramming somatic cells to the pluripotent state and differentiating these cells through the intermediate mesoderm lineage to nephron progenitors have brought the prospect of generating patient-specific human kidney tissue within reach (Lam et al., 2013; Mae et al., 2013; Taguchi et al., 2014; Takahashi and Yamanaka, 2006; Takasato et al., 2014). While these proof-of-principle experiments have elegantly shown differentiation of nephron progenitors, the numbers of cells that they generate have been relatively modest and identification of procedures to expand these progenitors is still required for practical applications such as engraftment (Lam et al., 2013; Takasato et al., 2014).

The mammalian kidney develops by radial addition of new nephrons that form at the outermost cortex within a progenitor cell niche known as the nephrogenic zone. As the collecting duct branches, progenitor cell aggregates at the collecting duct tips known as cap mesenchyme are induced to differentiate into renal vesicles, polarized derivatives that are the earliest precursors of the epithelial components of the nephron (Mori et al., 2003). The continuous epithelial induction of nephron progenitor cells causes their depletion, necessitating a mechanism to balance progenitor cell renewal with epithelial differentiation, thus enabling multiple rounds of nephrogenesis. Focus on this question over the past 10 years led to the discovery of distinct cell phenotypes, or compartments, that comprise the cap mesenchyme and the specific signaling pathways on which these cells depend (FIG. 6A; Brown et al., 2013; Kobayashi et al., 2008; Mugford et al., 2009; Park et al., 2012).

The least differentiated nephron progenitor compartment is marked by the transcriptional coactivator CITED1 and transcription factor SIX2 (Boyle et al., 2008a; Self et al., 2006). Previous studies have identified essential functions of the BMP, FGF and WNT signaling pathways in regulating the balance between renewal and differentiation in these cells (Barak et al., 2012; Blank et al., 2009; Brown et al., 2011a; Brown et al., 2013; Carroll et al., 2005; Karner et al., 2011).

BRIEF SUMMARY OF THE INVENTION

Certain aspects of the invention provide a cocktail of growth factors and small molecules that target specific cell signaling pathways, the cocktail having been formulated to allow/promote the expansion of nephron progenitor cells within a defined culture system. A surprising advantage of the invention is that it overcomes the extremely difficult process of obtaining an adequate number of nephron progenitor cells with high purity to study kidney biology and develop cell based therapies for treatment of kidney disease. Thus, in certain aspects, the invention provides a method that provides a means to distribute adequate numbers of nephron progenitor cells, as well as the medium used to grow these cells, which are useful for scientists worldwide.

Contemplated applications of the compositions and methods of the instant invention include at least the following:

Expansion of mouse nephron progenitors for research purposes.

Enrichment and expansion of nephron progenitors from a mixed population of cell types derived from the embryonic kidney.

Enrichment and expansion of rare nephron forming stem cells from a mixed population of cell types derived from adult mouse or human kidneys.

Enrichment and expansion of mouse or human cells of renal lineages derived from induced pluripotent stem cells (iPS) for research purposes and stem cell therapies.

Expansion of progenitor or stem cells from organs other than the kidney.

In one aspect the invention provides a composition for expanding a mammalian progenitor cell population that includes FGF9, LDN-193189, CHIR 99021 and at least one of BMP7 and BMP4. Optionally, the mammalian progenitor cell population is a nephron progenitor cell population.

In one embodiment, the composition also includes ROCKi, optionally wherein ROCKi is present at 1 uM to 10 uM, optionally at 10 uM. In another embodiment, the composition includes at least one of IGF1, IGF2 and Heparin, optionally IGF1 is present at 5 to 100 ng/ml, in certain embodiments at 20 ng/ml; optionally IGF2 is present at 0.1 to 10 ug/ml, in certain embodiments at 2 ng/ml; optionally Heparin is present at 1 to 10 ug/ml, in certain embodiments at 1 ug/ml. In an additional embodiment, the composition also includes one or more of APEL or DMEM/F12+KOSR as media and/or matrigel or gelatin as ECM (extracellular matrix).

ROCKi (and/or Y-27632) is a cell-permeable, highly potent and selective inhibitor of Rho-associated, coiled-coil containing protein kinase (ROCK). Y-27632 inhibits both ROCKI (Ki=220 nM) and ROCKII (Ki=300 nM) by competing with ATP for binding to the catalytic site. (Davies et al., Ishizaki et al.)) Without ROCKi, cells formed clumps rather than monolayer, which may cause premature differentiation.

Heparin is required for FGF9 binding to its receptor, and the absence of Heparin results in improper FGF9 activity.

In one embodiment, FGF9 (glia activating factor) is present at 25 to 250 ng/ml, optionally at 200 ng/ml. FGF9 kept progenitors alive and in the CITED1+ renewal state. The absence of FGF9 resulted in death and loss of CITED1/SIX2 expression. It is contemplated that other FGFs could substitute for FGF9 in the current cocktail (e.g., FGF1, 2, 9, 16 and/or 20).

In another embodiment, BMP7 (Bone morphogenetic protein 7, aka osteogenic protein-1 or OP-1) is present at 5 to 100 ng/ml, optionally at 30 ng/ml. In an additional embodiment, BMP4 (Bone morphogenetic protein 4) is present at 5 to 100 ng/ml, optionally at 30 ng/ml. BMP7 and/or BMP4 were necessary for proliferation and maintenance of nephron progenitors. Absence of BMP4 and BMP7 resulted in death of the culture.

In a further embodiment, LDN-193189 (BMP inhibitor) is present at 5 nM to 300 nM, optionally at 75 nM. LDN-193189 blocks differentiation of progenitors to keep them in a renewal state. Absent LDN-193189, loss of CITED1 expression and loss of competence of progenitors to undergo differentiation was observed.

LDN193189 is a cell-permeable, highly potent and selective BMP pathway inhibitor that inhibits BMP type I receptors ALK2 (IC50=5 nM) and ALK3 (IC50=30 nM), but not ALK4, ALK5, and ALK7 (>0.5 µM). It prevents Smad1, Smad5, and Smad8 phosphorylation. It is a useful compound for modulating stem cell differentiation (for example, neural differentiation of human ESC/iPSC in combination with SB431542). It was also used in animal models to treat FOP and ectopic ossification, as well as NSCLC lung cancer.

In another embodiment, the composition includes CHIR 99021, optionally present at 100 nM to 10000 nM, e.g., at 1 uM.

CHIR 99021 is a GSK-3β inhibitor. CHIR99021 has been shown to allow for long-term expansion of murine embryonic stem cells in a chemically-defined medium in conjunction with MEK/MAPK inhibitor PD184352 and fibroblast growth factor receptor (FGFR) inhibitor SU5402. CHIR 99021 is a canonical WNT agonist, necessary to promote proliferation. Cells do not proliferate and expand in the absence of CHIR99021.

In another embodiment, IGF1 (Insulin-like growth factor 1 (also called somatomedin C) is present at 20 ng/ml. In an additional embodiment, IGF2 (Insulin-like growth factor 2) is present at 2 ng/ml. IGF1 and IGF2 activate Pi3K, a known pathway for CITED1 progenitor maintenance. The absence of either IGF1 or IGF2 results in decreased proliferation.

Another aspect of the invention provides a method for expanding a mammalian progenitor cell population that involves: obtaining a mammalian progenitor cell population, and contacting and incubating the cell population with a composition of the invention for sufficient time to allow for expansion of the mammalian progenitor cell population.

Optionally, the mammalian progenitor cell population is a nephron progenitor cell population.

In certain embodiments, the mammalian progenitor cell population is expanded at least 10-fold, at least 100-fold, at least 1000-fold or at least 5000-fold. Optionally, the mammalian progenitor cell population is expanded 256-fold or 4096-fold.

In one embodiment, the mammalian progenitor cell population is derived from embryonic stem cells. Optionally, the mammalian progenitor cell population is human. In other embodiments, the mammalian progenitor cell population is murine.

In certain embodiments, the expanded mammalian progenitor cell population includes functional nephron cells.

In one embodiment, incubating occurs for at least 18 hours. Optionally, the mammalian progenitor cell population has a doubling time of 18 hours.

In another embodiment, the incubating occurs for at least 2, 4, or 9 days.

In a related embodiment, the cells are passaged every three days after four doublings.

Another aspect of the invention provides a method for expanding a mammalian progenitor cell population within a mammalian stem cell population that involves obtaining a mammalian stem cell population that includes mammalian progenitor cells, and contacting and incubating such a stem cell population with a compound of the invention for a time sufficient to allow for expansion of the mammalian progenitor cell population within the mammalian stem cell population.

In certain embodiments, the mammalian progenitor cell population (e.g., mammalian nephron progenitor cell population) is expanded at least 2-fold, at least 5-fold, at least 10-fold and/or at least 20-fold within the mammalian stem cell population.

In a related embodiment, the mammalian progenitor cell population is initially present at less than 5% within the mammalian stem cell population. In one embodiment, the mammalian progenitor cell population makes up at least 50% of all cells after incubating of the mammalian stem cell population with a composition of the invention for a time sufficient to allow for expansion of the mammalian progenitor cell population within the mammalian stem cell population.

Optionally, the mammalian stem cell population is human. In a related embodiment, the mammalian progenitor cell population is human.

In one embodiment, the expanded mammalian progenitor cell population includes functional nephron cells.

BRIEF DESCRIPTION OF THE DRAWINGS

FIG. 2 shows a listing of a complete nephron progenitor cell expansion cocktail recipe of the invention.

FIG. 5 shows that nephrons exhibiting key features of naturally occurring nephrons arose from expanded nephron progenitor cells. The left panel shows nephrons produced using the compositions and methods of the invention, while the right panel shows naturally occurring nephrons for comparison.

FIG. 6A shows another schematic of cap mesenchyme compartments and key signaling pathways required for their maintenance and differentiation. FIG. 6B shows Cited1creERT2-EGFP kidneys harvested at postnatal stages. Fluorescent imaging of GFP expression in cap mesenchymes "C" shown. FIG. 6C shows immunostaining of pSMAD1/5 (arrows) in kidney sections isolated from E17.5 to P1 (arrows). Cap mesenchymes are outlined with dotted red lines. FIG. 6D shows a pSMAD1/5 immunoblot of NZCs after intraperitoneal injection of P0 pups with either vehicle or 3 mg/kg of LDN twice daily until P2. Percent remaining after LDN treatment quantified in graph. NZCs were isolated from 4 kidney pairs per treatment group and pooled. FIG. 6E shows fluorescent imaging of kidneys from Cited1 or Six2 EGFP reporter mice in vehicle and LDN treated animals. Representative image from 4 kidney pairs per group shown. FIG. 6F shows cap mesenchyme marker analysis of isolated nephrogenic zone cells by qPCR. Data represent the mean±SD of qPCR technical replicates from 5 (DMSO) and 6 (LDN) pooled kidney pairs.

FIG. 7A shows CITED1 immunostaining of freshly plated monolayer cultures of purified progenitors isolated at developmental time points. FIG. 7B shows quantitation of CITED1+ progenitor purity from images shown in FIG. 7A. FIG. 7C shows stereo microscopy and GFP expression of purified CITED1+ progenitors in aggregate culture isolated from Cited1creERT2-EGFP kidneys and treated with CHIR (3 µM) and LDN (75 nM).

FIG. 8A shows immunostaining of CITED1+ progenitors isolated from E17.5 kidneys and expanded in NPEM through passage 3. DAPI is shown in blue. FIG. 8B shows stereo microscopy of aggregate cultures derived from CITED1+ progenitors cultured in monolayer in NPEM for 3 passages. Corresponding H&E staining of differentiated aggregates showed epithelial tubules (T) with lumens (bottom). FIG. 8C shows time course images of expanded CITED1+ progenitors differentiated in aggregate culture. FIG. 8D shows the number of CITED1+ progenitors present after each 3 day culture period with 50,000 cells per cm2 seeding density. FIG. 8E shows the number of CITED1+ progenitors present at the end of passage 0 (9 days) when plated at a low seeding density (250 cells/cm$^2$). FIG. 8F shows that GFP expression and lotus lectin (LTL) staining of CITED1+ progenitors expanded 2400 fold (from experiment in FIG. 8E) and transferred to aggregate culture.

FIGS. 9A to 9F show that slow cycling late nephron progenitors expanded and retained differentiation potential. FIG. 9A shows immunostaining of CITED1+ progenitors isolated from P1 kidneys and cultured in NPEM through passage 6. DAPI is shown in blue. FIG. 9B shows corresponding aggregate cultures derived from cell passages shown in FIG. 9A. FIG. 9C shows the percent of CITED1+ cells remaining after each passage. FIG. 9D shows the number of CITED1+ progenitors present after each 3 day culture period with 50,000 cells per cm$^2$ seeding density. FIG. 9E shows the expression of cap mesenchyme transcripts of freshly isolated CITED1+ progenitors. FIG. 9F shows Wnt4 expression in CITED1+ progenitors starved in keratinocyte basal medium and treated with BIO (0.5 µM) for 6 hours. Average values±SEM in FIGS. 9E and 9F shown.

FIG. 10A shows flow cytometry histogram of CITED1+ progenitors isolated from Cited1creERT2-EGFP reporter mice propagated in complete NPEM or in the absence of the indicated factors. FIG. 10B shows quantitation of GFP intensity (GFPHI or GFPLO/NEG) by flow cytometric analysis was used to quantify progenitor cell state in the absence of individual factors. FIG. 10C shows pSMAD1/5 immunostaining of CITED1+ progenitors grown in NPEM with and without LDN or BMP. FIG. 10D shows Cv2 expression in CITED1+ progenitors grown in NPEM in the presence (complete) and absence of LDN over 72 hours. Mean±SD shown. FIG. 10E shows aggregate culture of CITED1+ progenitors isolated from Cited1creERT2-EGFP reporter mice that were initially expanded for 3 days in monolayer in the presence or absence of LDN. FIG. 1OF shows immunostaining of CITED1+ progenitors expanded in NPEM for 3 days in the presence or absence of LDN.

FIGS. 11A to 11F show that NPEM supported clonal expansion of functional nephron progenitors from a heterogeneous CITED1+ pool. FIG. 11A shows SIX2 immunostaining of isolated NZCs (pass 0 and 2) and CITED1+ progenitors (pass 2) expanded in NPEM. FIG. 11B shows stereo microscopy and immunostaining of single cell derived colonies obtained from NZCs seeded in NPEM. FIG. 11C depicts a graphical representation of cell doublings in colonies seeded by single CITED1+ progenitor. FIG. 11D shows the number of cells recovered (black bars, left y-axis) and percent CITED1+ (white boxes, right y-axis) of single cell seeded colonies after passage 1. FIG. 11E shows phase contrast (left) and lotus lectin immunostain (right) of 24 clones (from FIG. 11D) differentiated with CHIR (3 µM) in aggregate culture. FIG. 11F shows stereo (top) and confocal (bottom) microscopy of an aggregate derived from a single CITED1+ progenitor after propagation in NPEM for 23 days through 2 passages (LTL—lotus lectin).

FIGS. 12A to 12H show that human embryonic stem cell derived nephron progenitors expanded in NPEM medium retained their capacity for organotypic epithelial differentiation. FIG. 12A shows CITED1 and PAX2 immunostaining of cells differentiated for 10 days from H9 hESCs using conditions reported previously by Takasato et al., 2014. FIG. 12B shows CITED1 and PAX2 immunostaining of cells differentiated using the Takasato procedure and expanded in NPEM. FIG. 12C shows PAX8 immunostaining of ES cell derived progenitors expanded in NPEM with and without LDN treatment at passage 1. FIG. 12D shows stereo microscopy of cells differentiated using the Takasato procedure and transferred to aggregate cultures containing CHIR. White boxes circle areas of epithelialization. FIG. 12E shows stereo microscopy of cells differentiated using the Takasato procedure, expanded in NPEM and transferred to aggregate cultures containing CHIR. Lotus lectin immunostaining (boxed regions, insets) shown in red. FIG. 12F shows H&E staining of CHIR treated aggregate cultures containing cells expanded in NPEM (pass 2) show extensive formation of tubules (T) with lumens (arrows). FIG. 12G shows lotus lectin and E-cadherin immunostaining of CHIR treated aggregate cultures containing cells expanded in NPEM (pass 2). FIG. 12H shows lotus lectin and PAX8 immunostaining of CHIR treated aggregate cultures containing cells expanded in NPEM (pass 2).

FIG. 13A shows the impact when individual factors were removed from NPEM and purified CITED1 progenitors from Cited1creERT2-EGFP×ICR mice were cultured in monolayer for 3 days. Cultures contained a 50/50 starting mix of GFP+ and GFP− cells. Top panels: Phase microscopy of cell morphology after 3 days in the absence of individual factors. Bottom panels: Corresponding immunofluoresence of GFP signal after 3 days in culture. FIG. 13B shows GFP immunofluorescence and corresponding light microscopy of 3D aggregates grown for 1 and 4 days respectively. Individual factors were removed from NPEM and purified CITED1 progenitors from Cited1creERT2-EGFP×ICR mice were cultured for 3 days in monolayer culture. Cells were dissociated and spotted in 3D aggregate on floating filters for the indicated times. Top panels: Vehicle only control shown after 1 day in culture. Bottom panels: Tubulogenesis can be seen when cultures are treated with CHIR, except when monolayer cultures were grown in the absence LDN. 3 monolayer replicates were pooled per 3D aggregate. 1 of 2 experimental replicates shown. Note: FGF9 and BMP4/7 minus cultures died during the monolayer phase.

In FIG. 15A, progenitors were purified from nephrogenic zone cells isolated from E13.5 kidneys, and showed CITED1+ enrichment. In FIG. 15B, purified CITED1 progenitors expanded in NPEM for 3 days retained expression of CITED1, SIX2, but not LEF1 protein. In FIG. 15C, purified CITED1 progenitors expanded in monolayer cultures with NPEM containing LDN underwent differentiation when transferred to 3D aggregate culture for 7 days after treatment with a high dose of CHIR (left panels). CITED1 progenitors expanded in monolayer cultures with NPEM, but without LDN lost their potential to differentiate (right panels).

FIGS. 17A and 17B show a test of the ability of clones expanded from a single cell to undergo tubulogenesis before and after passage. FIG. 17A shows single cells derived from a bulk population of CITED1 progenitors, which were seeded and grown in NPEM for 12 days. Colonies were dissociated, passed directly to 3D aggregate culture and treated with CHIR for 7 days. Aggregates were imaged by light microscopy, fixed and stained with lotus lectin (red) and DAPI (blue). Aggregates derived from 8 clones expanded in monolayer shown. Cell count distribution of 28 single cell derived colonies on day 12 are shown in the graph to the right. FIG. 17B shows a single cell derived colony that was dissociated on day 11, counted and cultured in monolayer for 2 more days before being passaged to 3D aggregate culture and treated with CHIR for 7 days. Aggregate imaged by light microscopy and fixed and stained with lotus lectin (red) and DAPI (blue). Cell count distribution of 24 single cell derived colonies on day 13 shown in the graph to the right.

In FIG. 18A, nephron progenitor cells immunostained for SIX2 and WT1 were differentiated for 5 days from H9 hESCs using the conditions reported by Takasato et al and switched to NPEM for an additional 5 days (top panels). Cells differentiated using the Takasato procedure for 10 days (bottom panels). In FIG. 18B, Cells differentiated using the Takasato procedure were switched to NPEM after 5 days and expanded for 2 passages (1:8 split) with retained expression of WT1 and SIX2.

In FIG. 19A, passage 3 progenitors were grown in NPEM in the absence of individual factors for 3 days in monolayer culture and immunostained for CITED1, SIX2, PAX2 and WT1. Antibody staining is shown in red and nuclear counterstaining with DAPI is shown in blue. In FIG. 19B, passage 3 progenitors were grown in NPEM in the absence of the indicated factors for 3 days in monolayer culture and immunostained for PAX2.

DETAILED DESCRIPTION OF THE INVENTION

Figure 1:
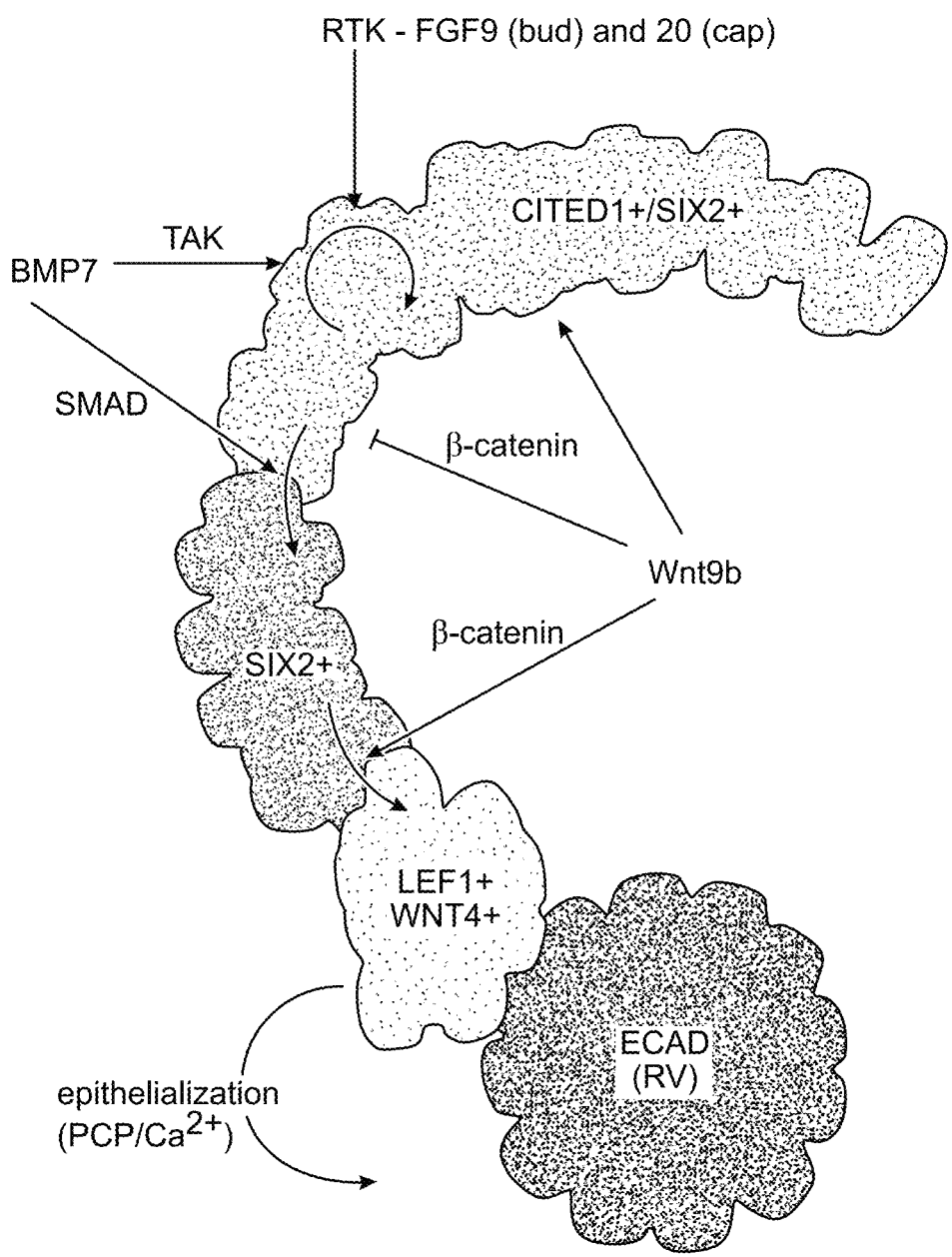
FIG. 1 shows a model from nephron progenitor cell expansion studies.
Figure 3:
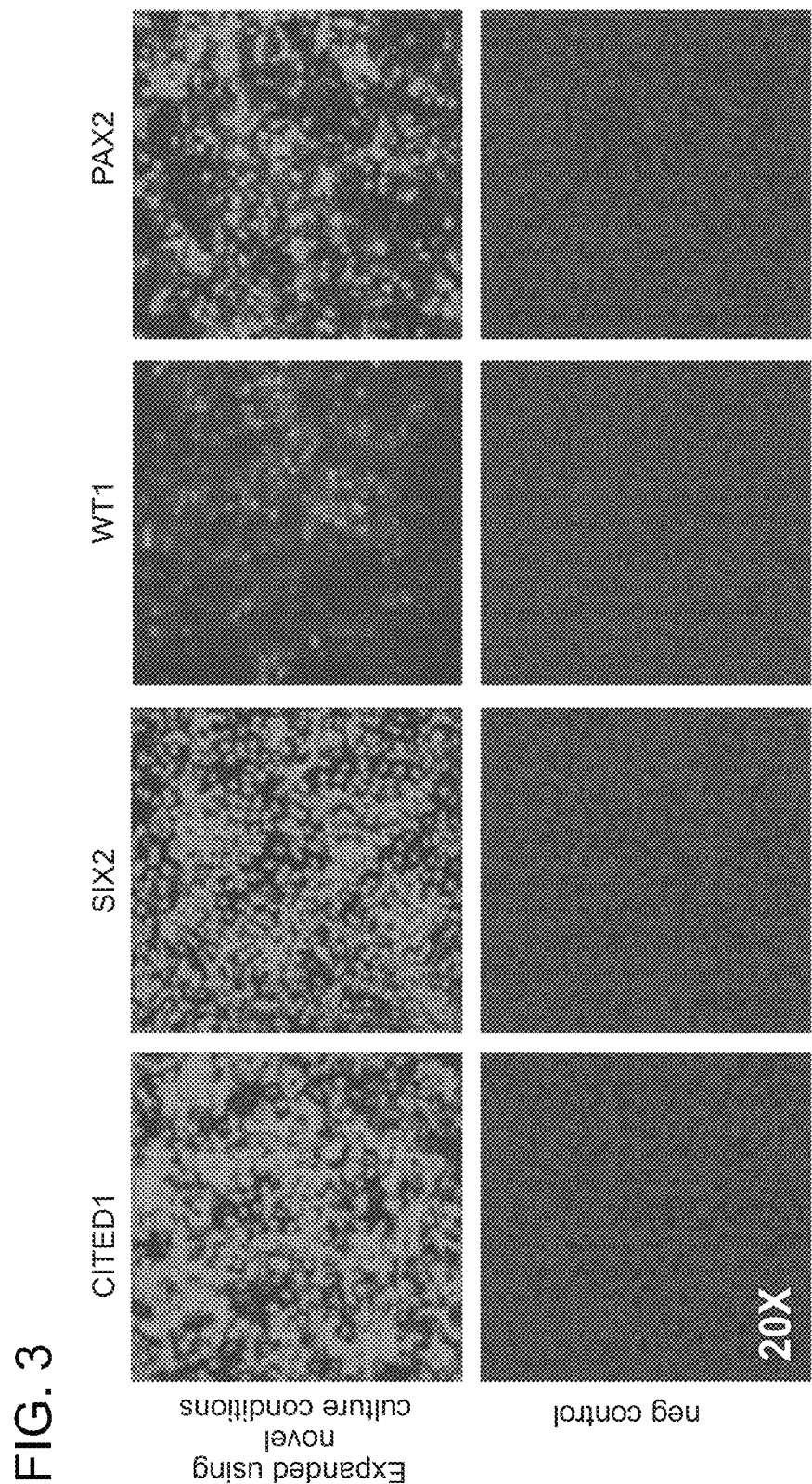
FIG. 3 shows that the medium formulation of the invention successfully expanded nephron progenitor cells in culture, retaining expression of hallmark nephron progenitor markers. Thus, Nephron progenitor cells were shown to be expanded 256 fold (2 million to 500 million cells with retained molecular marker profile.
Figure 4:
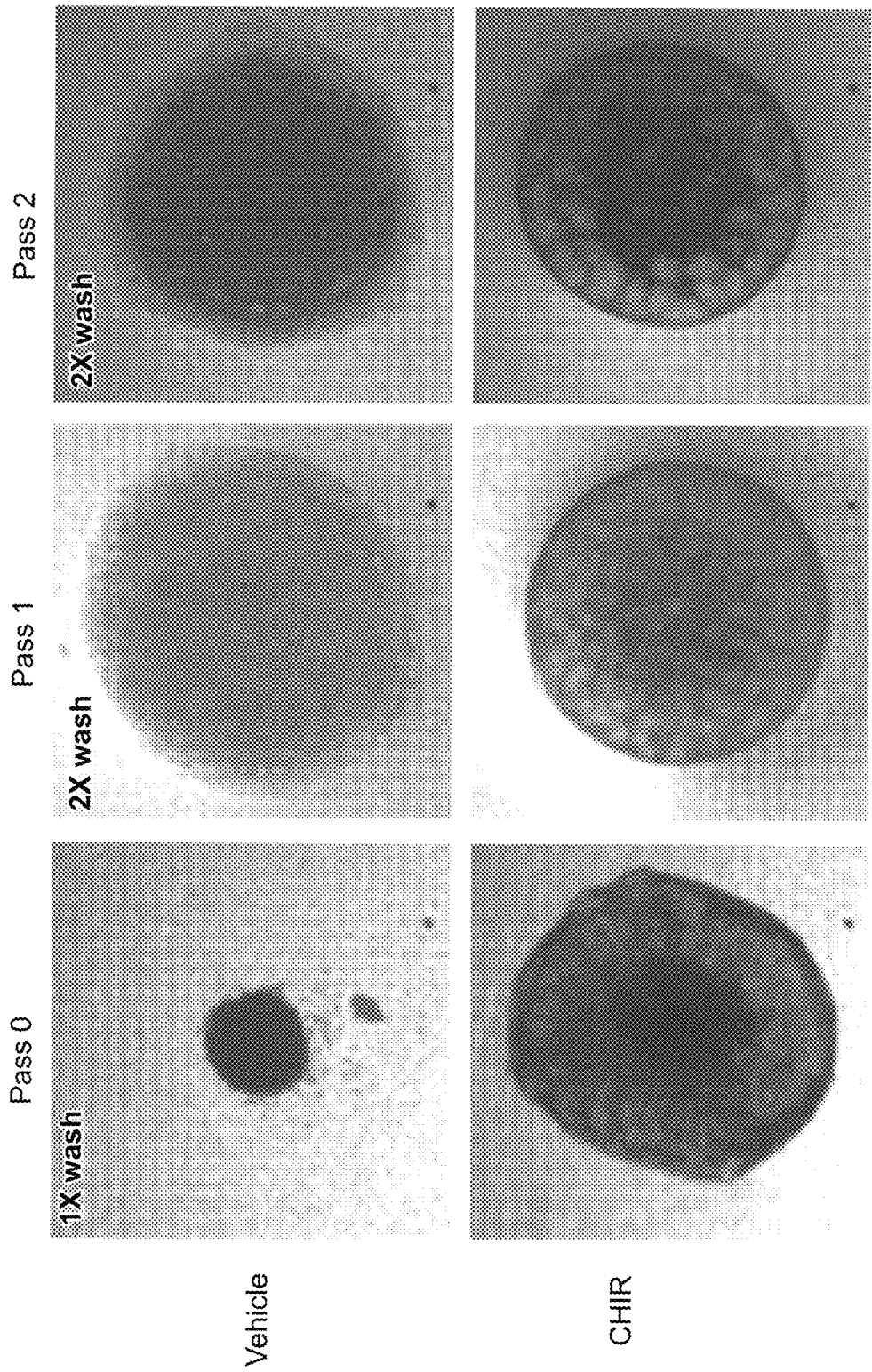
FIG. 4 shows that nephron progenitor cells formed nephron tubules following expansion. Thus, progenitors expanded using the disclosed method(s) retained their capacity for functional differentiation.

The present invention is based on the discovery of a cocktail formulation capable of expanding nephron progenitor cells in culture.

FGF, BMP and WNT have been identified to balance embryonic nephron progenitor cell renewal and differentiation. By modulating these pathways, an in vitro niche was remarkably discovered in which nephron progenitor cells from embryonic kidneys or derived from human embryonic stem cells could be propagated. Nephron progenitor cell cultures expanded several thousand-fold in this environment could be induced to form tubules expressing nephron markers. Single cell culture revealed phenotypic variability within the early CITED1− expressing nephron progenitor cell compartment, indicating that it included a mixture of cells with varying progenitor potential. Furthermore, it was found that the developmental age of nephron progenitor cells did not correlate with propagation capacity, indicating that cessation of nephrogenesis was related to factors other than an intrinsic clock. This in vitro nephron progenitor niche has been identified to possess important applications for expansion of cells for engraftment and can facilitate investigation of mechanisms that determine the balance between renewal and differentiation in these cells.

It was specifically explored herein if current understanding of the signaling environment for nephron progenitor cells was sufficient to allow for its reconstruction by manipulation of reported signaling pathways ex vivo. CITED1+/SIX2+ cells were used in a screening strategy to combinatorially test the potential of known nephrogenic zone signaling pathways to promote nephron progenitor renewal. It was remarkably identified that CITED1+/SIX2+ cells could be propagated in an undifferentiated state, yet retain the potential for epithelial differentiation. Thus, using a combination of recombinant proteins and small molecules, it was possible to functionally recapitulate conditions in the nephrogenic zone. Furthermore, these conditions could be extrapolated to human embryonic stem cell (hESC)-derived nephron progenitor cells, which also retained both their progenitor cell phenotype and their potential for epithelial differentiation. Hence, in addition to functionally recapitulating the signaling environment of the nephrogenic zone using a predictive approach, a method was developed for expanding undifferentiated yet functionally competent human nephron progenitor cells for nephron regeneration experiments.

Factors used in the media of the invention include FGF9, heparin, BMP4 and 7, LDN-193189, CHIR99021, Y-27632, IGF1 and 2, Matrigel and APEL. Further detail regarding each of these components is provided in the following table:

TABLE 1

Summary of factors used in nephron progenitor expansion medium (NPEM)

| Factor | Working dose | Function | References |
|---|---|---|---|
| FGF9 | 200 ng/ml | Renewal and proliferation | (Barak et al., 2012; Brown et al., 2011a) |
| Heparin | 1 ug/ml | FGF signaling activity | (Venkataraman et al., 1996) |
| BMP4 and 7 | 30 ng/ml each | proliferation | (Blank et al., 2009) |
| LDN-193189 | 75 nM | SMAD inhibitor of differentiation | (Yu et al., 2008) |
| CHIR99021 | 1 µM | WNT agonist, renewal and proliferation | (Karner et al., 2011) |
| Y-27632 | 10 µM | ROCK inhibitor, survival during plating | (Tsutsui et al., 2011; Watanabe et al., 2007) |
| IGF1 and 2 | 20 ng/ml & 2 ng/ml | Cell growth and proliferation | (Bach and Hale, 2014; Rogers et al., 1999) |
| Matrigel | 1:25 dilution | ECM, cell attachment | (Takasato et al., 2014) |
| APEL | 1X | Basal stem cell medium | (Takasato et al., 2014) |

The instant invention is based at least in part, upon the discovery that the nephrogenic zone cell signaling environment could be recreated in vitro for extensive propagation of undifferentiated nephron progenitor cells. Modulation of FGF, BMP, WNT and ROCK signaling pathways was necessary to maintain cells in the CITED1+ state with epithelial differentiation potential. This appears to constitute the first completely defined culture system for the expansion of functionally competent nephron progenitors. Importantly, this system can be used for the expansion of embryonic stem cell-derived human nephron progenitor cells. Cell signaling requirements for mouse and human nephron progenitor cells were similar in all aspects except the requirement for BMP. Subtraction of BMP from the culture medium of human cells resulted in only a partial loss of the progenitor marker profile compared to the complete loss observed for mouse progenitors. Published differentiation protocols for human embryonic stem cells generate at most 50% nephron progenitor cells, and approximately half of the culture remained undefined (Lam et al., 2013; Mae et al., 2013; Takasato et al., 2014). Without wishing to be bound by theory, it therefore appears likely that cells in the culture may have been producing BMPs and other factors that masked the effects of BMP7 withdrawal. Development of purification procedures for human nephron progenitor cells are necessary to directly compare the signaling requirements of derived human nephron progenitor cells with CITED1+ cap mesenchyme cells.

BMP Signaling in Nephron Progenitor Cell Maintenance

FGF, BMP and WNT each influence renewal and differentiation of the nephron progenitor cell, but how the cell interprets these signals depends on its differentiation state, as well as concurrent signaling from the surrounding niche (Brown et al., 2013; Das et al., 2013; Fetting et al., 2014; Karner et al., 2011). BMP7 promotes nephron progenitor proliferation through a MAPK pathway, whereas pSMAD signaling transitions progenitors out of the CITED1+ compartment (Blank et al., 2009; Brown et al., 2013). Molecular mechanisms that determine the balance of MAPK versus pSMAD activation by BMP7 in nephron progenitors are not understood. However, recent data have suggested that FGF signaling through PI3K/MAPK may repress pSMAD1/5 signaling in unprimed cap mesenchyme (Motamedi et al., 2014). In the cultures disclosed herein, pSMAD1/5 persisted in the presence of exogenously added FGF9, indicating that additional niche factors present in the developing organ were required for FGF-mediated suppression of pSMAD in the CITED1+ compartment. A key factor in the development of the instant culture procedure was the addition of the small molecule LDN, which blocked pSMAD activity and prevented progenitors from exiting the CITED1+ compartment, while still allowing proliferation and survival signals provided by BMP stimulation.

Functional Heterogeneity within the CITED1+ Progenitor Population

Gene expression profiling of the CITED1+ cap mesenchyme indicated that this was not a homogenous cell population (Mugford et al., 2009). Meox1 and Dpf3 were expressed in a specific subpopulation of CITED1+ progenitors adjacent to the more differentiated CITED1−/SIX2+ compartment and were not expressed in CITED1+ progenitors in more cortical cap mesenchyme. While the functions of these transcription factors during kidney development remain unknown, without wishing to be bound by theory, their localized expression indicated that the CITED1+ population might be phenotypically heterogeneous, perhaps with one renewing subcompartment, and one sub-compartment in the process of exiting the CITED1+ state. The instant analysis of single cells cultured for 5 days revealed a largely binomial distribution of cellular doubling, supporting functional heterogeneity of the CITED1+ cap mesenchyme population. Clones derived from the most rapidly dividing group could be expanded to several hundred thousand cells that retained the potential for epithelial differentiation. Without wishing to be bound by theory, it therefore appeared probable that these highly proliferative clones derived from cells within the CITED1+ compartment with extensive progenitor potential that might function as "super progenitors" from which the bulk of CITED1+ cap mesenchyme cells were derived. Lineage analysis of the cap mesenchyme using a tamoxifen-inducible Cited1-creERT2;Rosa26R strain showed that a high proportion of cells labeled at E13.5 were retained in the cap mesenchyme at E19.5, indicating the presence of a self-renewing sub-population (Boyle et al., 2008b). An alternate possibility is that the instant medium formulation provided an advantage to more differentiated cells within the CITED1+ compartment. In support of this, CITED1+ progenitors derived from P1 kidneys could be expanded considerably further than those derived at E17.5, while having a lower proliferative index and higher levels of Meox1. Single cell transcriptome analysis coupled with phenotyping of a large number of cap mesenchyme cells is contemplated for discernment of the biological basis for the heterogeneity that was observed within the CITED1+ population.

The Nephrogenic Niche Regulates Nephron Progenitor Lifespan

Recent high resolution studies have indicated that cap mesenchyme displays progressively decreased proliferation and thinning throughout development until it is depleted (Short et al., 2014). Based upon this model and the average cell cycle lengths calculated for the cap mesenchyme (33 hours at E17.25), E17.5 progenitors in the CITED1+ compartment would on average be expected to expand no more than 2 doublings prior to cessation. However, in isolation, differentiation-competent CITED1+ progenitors were able to divide in bulk 9 times. Those that had undergone limiting dilution and selection could double even further, up to 17 times. Furthermore, CITED1+ progenitors isolated at P1, while possessing a lower proliferative index as expected, underwent more than 12 doublings in bulk culture. If progenitor renewal was internally regulated by a predetermined biological clock that counted the number of divisions, it would be expected to observe cells isolated from E17.5 to double more than those isolated at P1, but this was not the case. Instead, without wishing to be bound by theory, it was contemplated that the reduced rate of proliferation in the P1 cells might underlie their depletion, perhaps because epithelial induction by collecting duct tips was not reduced proportionally, leading to cap mesenchyme exhaustion. Alternately, these findings might indicate that the niche, rather than an internal clock, determined the number of doublings a CITED1+ cell could undertake. Removing the cells from this niche would relieve this signal, resulting in similar proliferative capacity for cells isolated at different developmental stages.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of the mixtures described herein toward recapitulating the signaling environment of the nephrogenic zone and/or expanding undifferentiated yet functionally competent human nephron progenitor cells. Therefore, the specific embodiments described herein are not limiting and one skilled in the art can readily appreciate that specific combinations of the agents described herein can be tested without undue experimentation toward identifying recapitulation of the signaling environment of the nephrogenic zone and/or expansion of undifferentiated yet functionally competent human nephron progenitor cells.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

This invention is further illustrated by the following examples which should not be construed as limiting. The contents of all references, patents, and published patent applications cited throughout this application, as well as the figures, are incorporated herein by reference.

EXAMPLES

Example 1

Experimental Procedures

Cell culture. CITED1+ progenitors were purified from NZCs derived from E17.5 kidneys as previously described (Brown et al., 2011b; Brown et al., 2013). CITED1+ progenitors were cultured in monolayer on hESC qualified Matrigel™ coated plates (Corning). For human or mouse passage, cells were dissociated by incubation with TrypLE (Life Technologies) for 2 minutes at 37 C, washed and spun 2× at 300 g in autoMACs running buffer (Miltenyi) prior to resuspension in NPEM as described in Table 1. NPEM is changed every 2 days. Cells were differentiated in aggregate culture with CHIR (3 µM) in medium as previously described (Brown et al., 2013).

Immunofluorescence and microscopy. Tissue sections, monolayer cultures and aggregates were immunostained as previously described (Blank et al., 2009; Brown et al., 2013). Antibodies were used at 1:100 dilution and include CITED1 (NeoMarkers); pSMAD1/5 (Cell Signaling Technology); SIX2 (Proteintech); LEF1 (Cell Signaling Technology); PAX2 (Proteintech); PAX8 (Proteintech); E-cadherin (BD Transduction Laboratories) and lotus lectin staining at 1:200 (Vector Laboratories). Live images of GFP+ progenitors from Cited1creERT2-EGFP mice in monolayer or aggregate culture were imaged with epi-fluorescent and fluorescent stereo microscopes, respectively.

Quantitative PCR. RNA purification, cDNA synthesis, and quantitative PCR were performed as previously described (Brown et al., 2011a). All raw data have been normalized to β-actin expression, and fold changes are relative to the vehicle control.

Flow cytometry. CITED1+ progenitors were purified from GFP+ kidneys isolated from Cited1creERT2-EGFP× ICR mice and cultured as described in the text. GFP fluorescence intensity and cell counts were collected on a FACSCalibur (BD) and data were analyzed using FlowJo software.

Statistical Methods

For qPCR, P-values shown were calculated using a two-tailed heteroscedastic Student's t-test and P<0.05 was considered significant. Error bars represent standard deviation for technical replicates derived from NZCs of 20-24 pooled kidneys or standard error for biological replicates derived from 3 independent mouse litters of pooled kidneys. For flow cytometry and cell count experiments, error bars represent average values±SD calculated from three culture well replicates. CITED1+ purity was determined from at least 3 independent images by normalizing to the number of DAPI-stained nuclei in each field using ImageJ with error bars representing the mean±SD.

Mouse strains and treatments. Animal care was in accordance with the National Research Council Guide for the Care and Use of Laboratory Animals and protocols were approved by the Institutional Animal Care and Use Committee of Maine Medical Center. CITED1 progenitors were derived from kidneys of Cited1creERT2-EGFP×ICR (Institute for Cancer Research mice) heterozygous mice. Cited1creERT2-EGFP and Six2cre-EGFP mouse strains are maintained on an FVB/NJ background (Boyle et al., 2008a; Kobayashi et al., 2008). Pregnant mice were injected at 12 hour intervals at the times indicated with 3 mg/kg LDN-193189 in 20 ul of DMSO/PBS.

Example 2

Figure 6A:
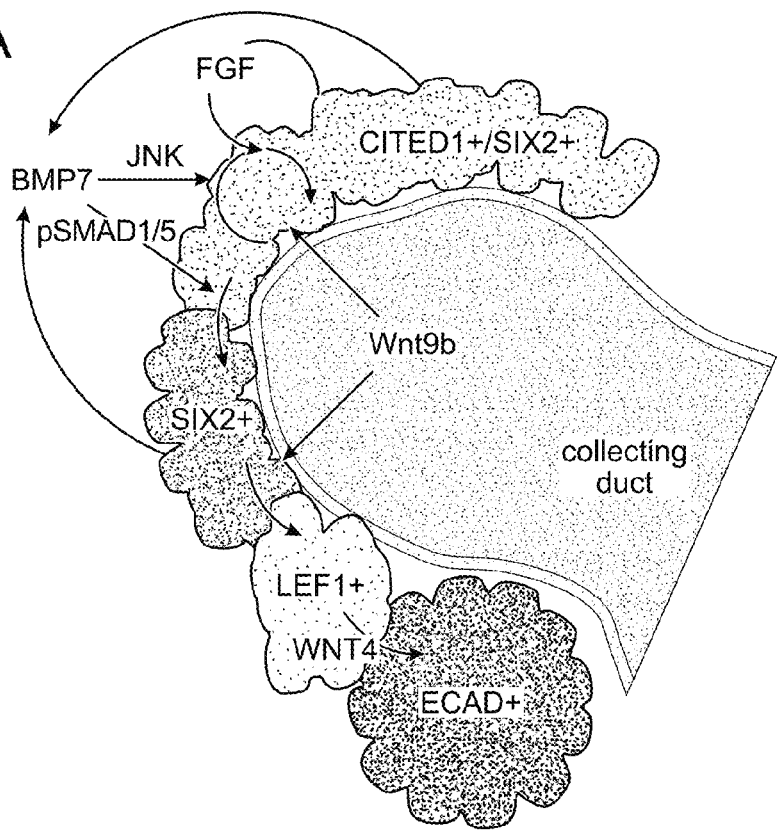
FIGS. 6A to 6F show that SMAD inhibition with LDN-193189 retained nephron progenitors in the CITED1 compartment in vivo.
Figure 6B:
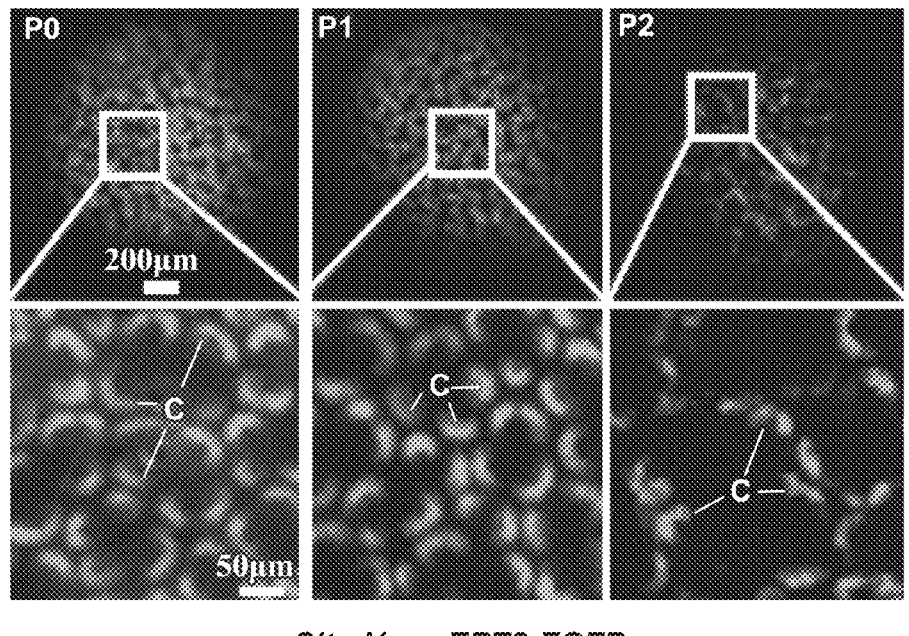
Figure 6C:
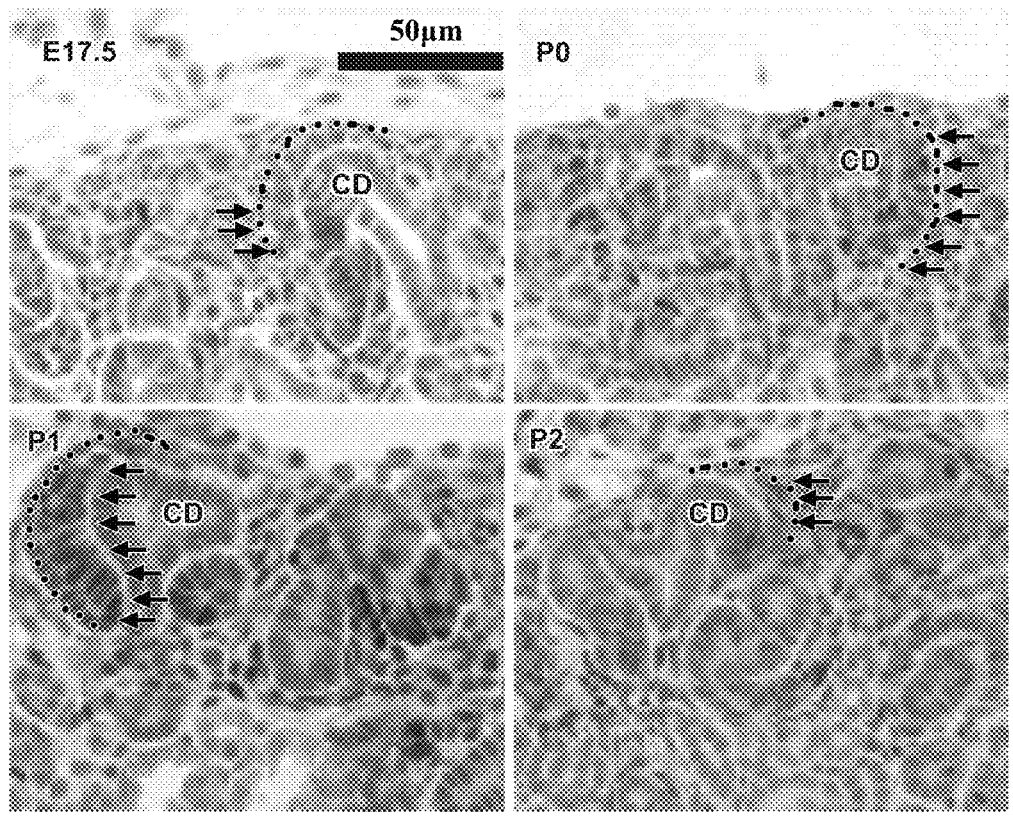

SMAD Inhibition with LDN-193189 Retained Nephron Progenitors in the CITED1-Expressing Compartment As a starting point for the development of conditions for propagation of nephron progenitor cells, a series of observations on signaling in cap mesenchyme during the terminal stage of nephrogenesis were drawn upon. It was previously shown that BMP7 signaling through the SMAD1/5 pathway was required for undifferentiated CITED1+/SIX2+ progenitors to transition to a CITED1−/SIX2+ state in which they are sensitized to epithelial induction by WNT/β-catenin signaling (FIG. 6A; Brown et al., 2013). In the mouse, cessation of nephrogenesis occurred shortly after birth and this was accompanied by a loss of Cited1+ cap mesenchyme by P2 (FIG. 6B). It was reasoned that SMAD1/5 signaling might have increased during the terminal phase of nephrogenesis, skewing the renewal versus differentiation balance and depleting the cap mesenchyme. Immunostaining of mouse kidneys from E17.5 to P2 for activated SMAD1/5 (pSMAD1/5) showed that this was indeed the case, and that increased SMAD1/5 activation in the cap mesenchyme associated with cessation of nephrogenesis (FIG. 6C).

Figure 6D:
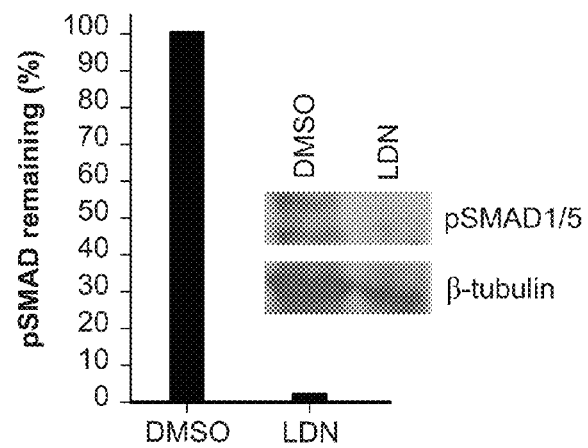
Figure 6E:
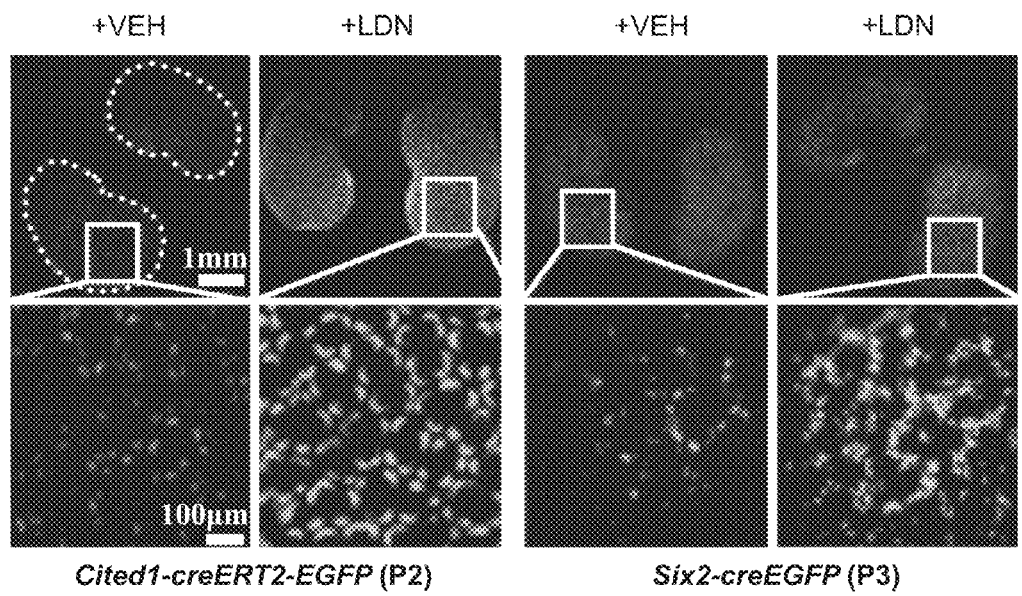
Figure 6F:
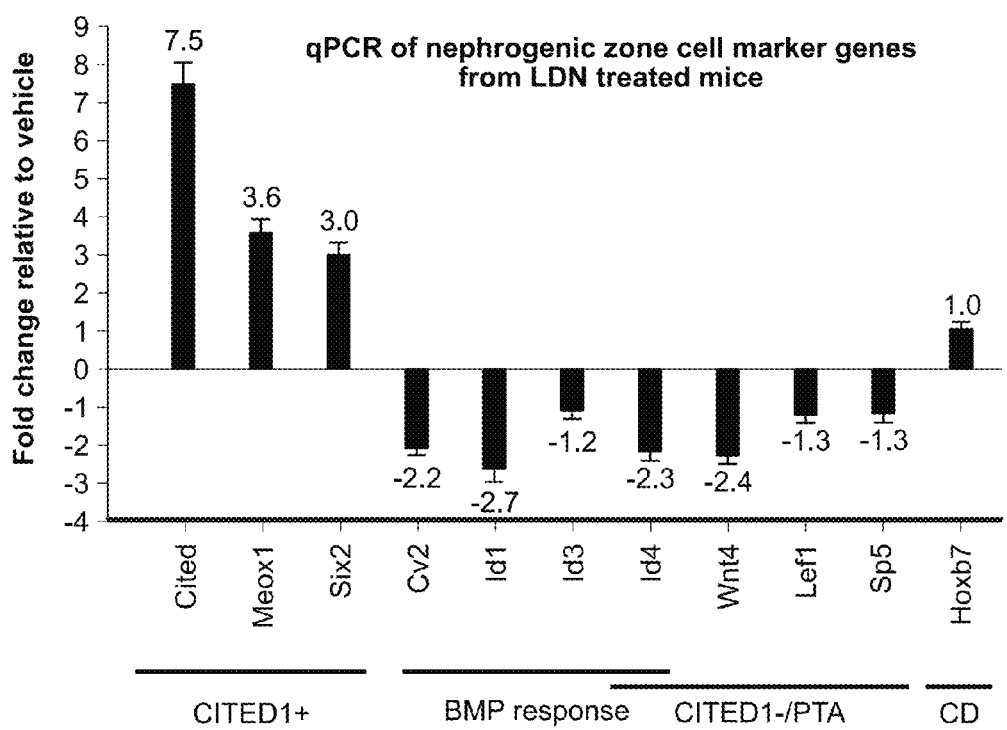

To understand if cap mesenchyme cells in their natural signaling environment could be prevented from transitioning out of the native CITED1+ progenitor cell state, newborn animals were treated with the SMAD1/5 small molecule inhibitor LDN-193189 (LDN) during the first two postnatal days. LDN was selected over other similar analogs because it is highly specific for SMAD1/5 and has been successfully used in vivo (Yu et al., 2008). Immunoblot of isolated nephrogenic zone cells (NZCs) from LDN-treated animals demonstrated greater than 95% reduction in SMAD1/5 phosphorylation compared to vehicle-treated controls (FIG. 6D). To measure the differentiation status of nephron progenitor cells, Cited1creERT2-EGFP and Six2cre-EGFP mouse strains were used, which dynamically expressed fluorescent protein under the control of Cited1 and Six2 (Boyle et al., 2008a; Kobayashi et al., 2008). While untreated animals lost expression of Cited1 and Six2 in cap mesenchyme at P2 and P3, respectively, expression was maintained in LDN-treated pups (FIG. 6E). RT-qPCR analysis of isolated nephrogenic zone cells with additional marker genes that are expressed within these two compartments supports the conclusion that the progenitor state had been rescued in LDN-treated cap mesenchymes (FIG. 6F). Expression of CITED1+/SIX2+ compartment-specific transcripts such as Cited1, Meox1 and Six2 and loss of markers for the CITED1−/SIX2+ and pretubular aggregate (PTA) compartments were observed, including the WNT/β-catenin response genes Wnt4, Lef1 and Spy. Transcription of BMP response genes including Crossveinless-2 (Cv2) and several Inhibitors of differentiation (Ids) was also decreased, consistent with a suppression of SMAD signaling by LDN (FIG. 6F). Thus, it was concluded that inhibition of pSMAD1/5 activation could retain cap mesenchyme cells in a Cited1+/Six2+ progenitor cell state within their natural signaling niche.

Figure 7C:
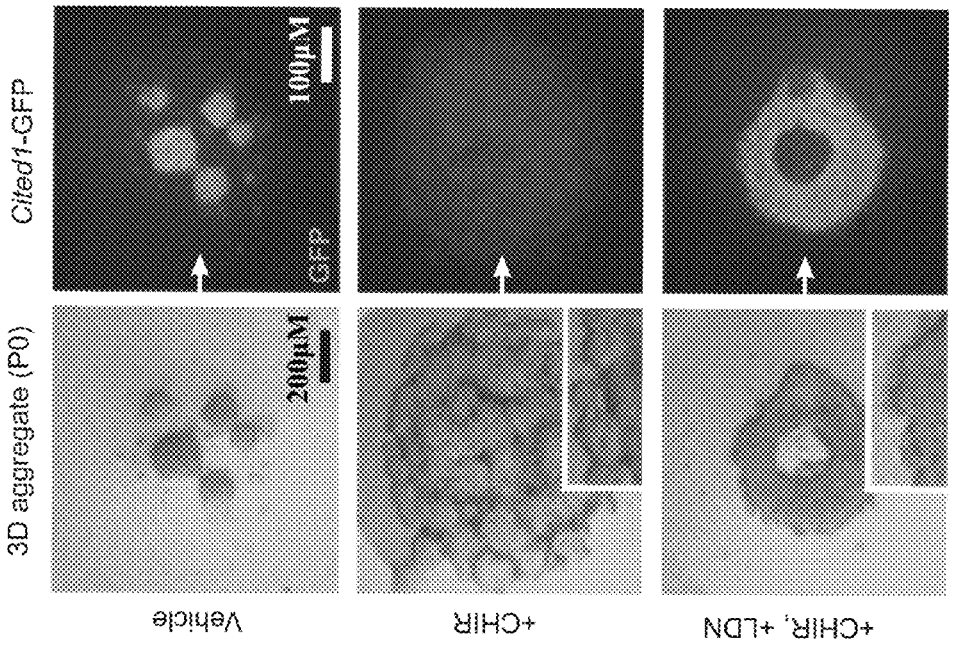
FIGS. 7A to 7C show SMAD inhibition with LDN-193189 retained nephron progenitors in the CITED1 compartment in vitro.
Figure 7A:
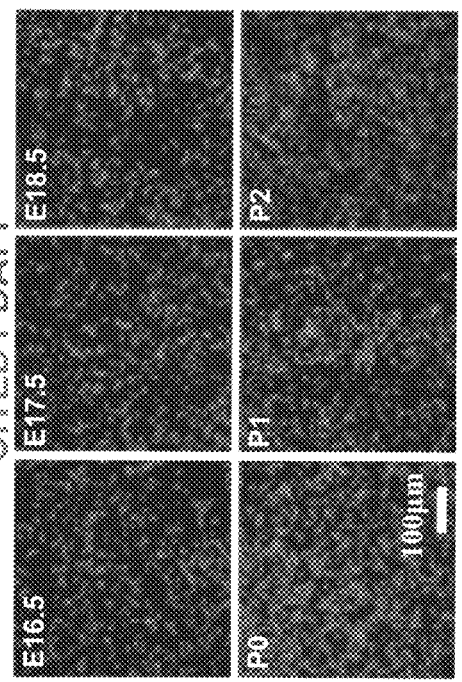
Figure 7B:
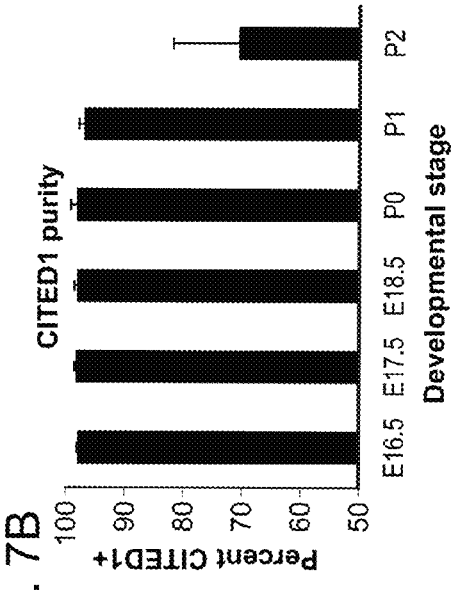

To understand if these observations could be extrapolated to CITED1+ cells in culture, a series of experiments was performed upon nephron progenitor cells isolated from embryonic mouse kidneys. Using a previously developed isolation protocol, CITED1+ progenitors were harvested from embryonic mouse kidneys between the ages of E16.5 to P1 at near 100% purity, allowing interrogation of the CITED1+ population at multiple time points (FIGS. 7A and 7B) (Brown et al., 2013). However, CITED1 progenitor purity dropped to 75% by P2, likely due to the loss of CITED1+ progenitors that occurred during cessation (FIG. 7B and FIG. 6B). When aggregated on polycarbonate filters at the air-liquid interface and cultured in serum free medium (aggregate cultures) in the presence of the WNT/β-catenin agonists BIO (2 μM) or CHIR99021 (CHIR, 3 μM), these progenitors underwent robust tubulogenesis, which was dependent on endogenously produced BMP ligand (Brown et al., 2013; Osafune et al., 2006). CITED1+ progenitors isolated from P0 Cited1creERT2-EGFP mice underwent tubulogenesis and lost GFP expression by day 4 of CHIR treatment (FIG. 7C). However, addition of LDN blocked tubulogenesis and maintained GFP expression. These results demonstrated that pSMAD1/5 inhibition could retain cultured progenitors in an undifferentiated Cited1+ state in the presence of active BMP and WNT/β-catenin signaling, indicating that LDN treatment would be required for in vitro propagation of these cells.

Example 3

Figure 8A:
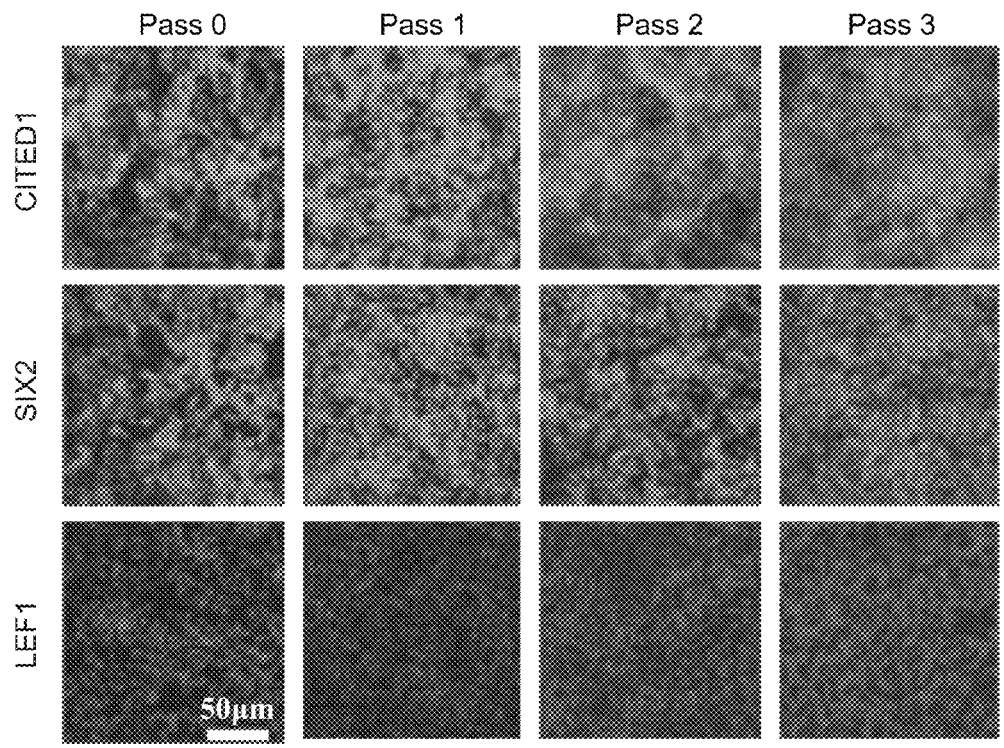
FIGS. 8A to 8F show that FGF, BMP and WNT expanded functionally competent CITED1+ nephron progenitors.

Developmental Regulators FGF, BMP and WNT were Required for Maintenance, Expansion and Differentiation of CITED1 Progenitors To define additional factors that were required for nephron progenitor propagation, past studies were consulted related to signaling in cap mesenchyme (Table 1). It was previously demonstrated that addition of either FGF1, 2, 9, or 20 promoted the maintenance and proliferation of CITED1 progenitors when cultured in monolayer on fibronectin coated wells with keratinocyte serum-free medium (Brown et al., 2011a). However, these cells lost expression of cap mesenchyme markers after 2 to 3 days and died. FGF9 was selected for use in monitoring CITED1 maintenance and proliferation, as it was recently identified as a natural ligand for maintenance of nephron progenitors in vivo (Barak et al., 2012). Heparin was included as it facilitates the binding of FGF9 to its receptor. It was previously shown that BMP activation of the JNK pathway was critical for the proliferation of mouse nephron progenitors (Blank et al., 2009). Although nephron progenitors expressed Bmp7, recombinant BMPs were included to counteract the dilution of endogenous BMP7 in the culture medium. To promote protein stability in the medium, BMP4 as well as BMP7 were also incorporated. These factors functioned equivalently in nephron progenitor cell renewal (Oxburgh et al., 2005). Low level WNT signaling was necessary for proliferation and renewal of CITED1 progenitors (Karner et al., 2011). Since LDN blocked cells from transitioning to the SIX2 only state in which they became sensitive to WNT-mediated epithelialization, it was possible to add a low dose of CHIR (1 μM) without promoting differentiation. The Rho kinase inhibitor Y-27632 was included because it increased the survival rate of dissociated stem cells during plating and passage and supported their long term maintenance (Tsutsui et al., 2011; Watanabe et al., 2007). Insulin like growth factors 1 and 2 (IGF1/2) were included because they promoted cell proliferation, inhibited cell death and were important for overall kidney growth and nephron endowment in rodents (Bach and Hale, 2014; Rogers et al., 1999). To ensure compatibility with hESC differentiation approaches, APEL was selected as the basal medium and Matrigel™ as the substrate because they have been used in the derivation of hESC-derived nephron progenitors (Takasato et al., 2014). When grown in this defined nephron progenitor expansion medium (NPEM), CITED1+ progenitors isolated from E17.5 mice maintained expression of CITED1/SIX2 and did not express the PTA marker LEF1 through 3 passages when split and plated at a constant cell density of 50,000 cells per cm2 (FIG. 8A). CITED1+/SIX2+/LEF1− cells proliferated vigorously at greater than 99% purity in our propagation conditions and by passage 2 there was a 1:512 expansion of the input cell number. Thus, approximately one billion undifferentiated nephron progenitor cells can be derived from two million purified CITED1+ cells that are typically isolated from a single litter of embryonic kidneys. Thus, the instant attempt to recapitulate the nephrogenic zone signaling environment for progenitor cells successfully allowed extensive propagation of undifferentiated cells.

Figure 8B:
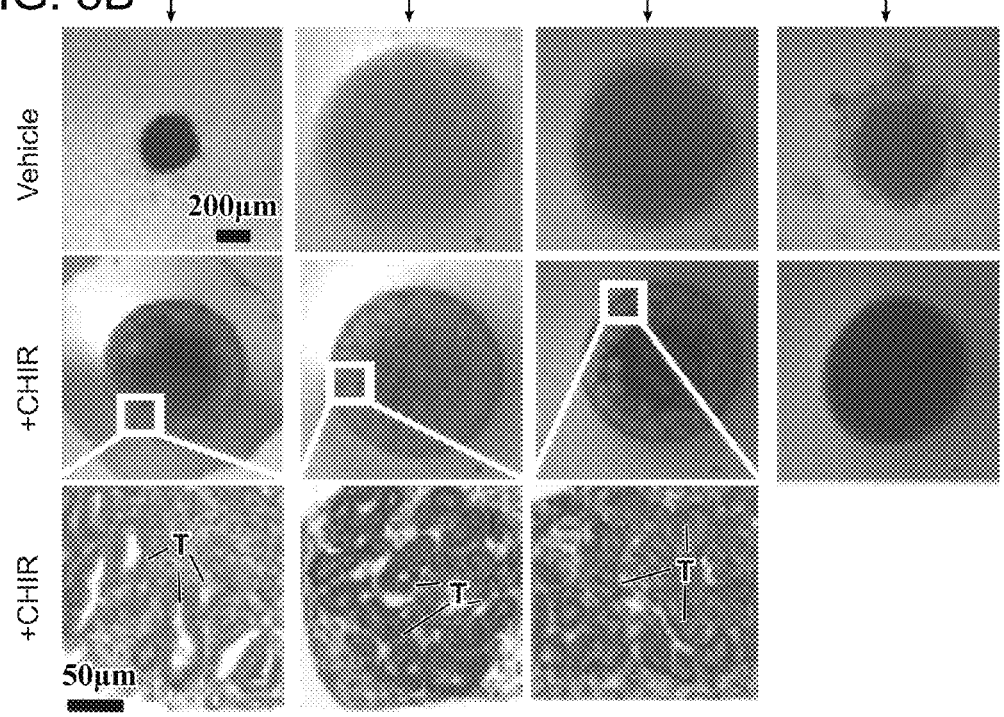
Figure 8C:
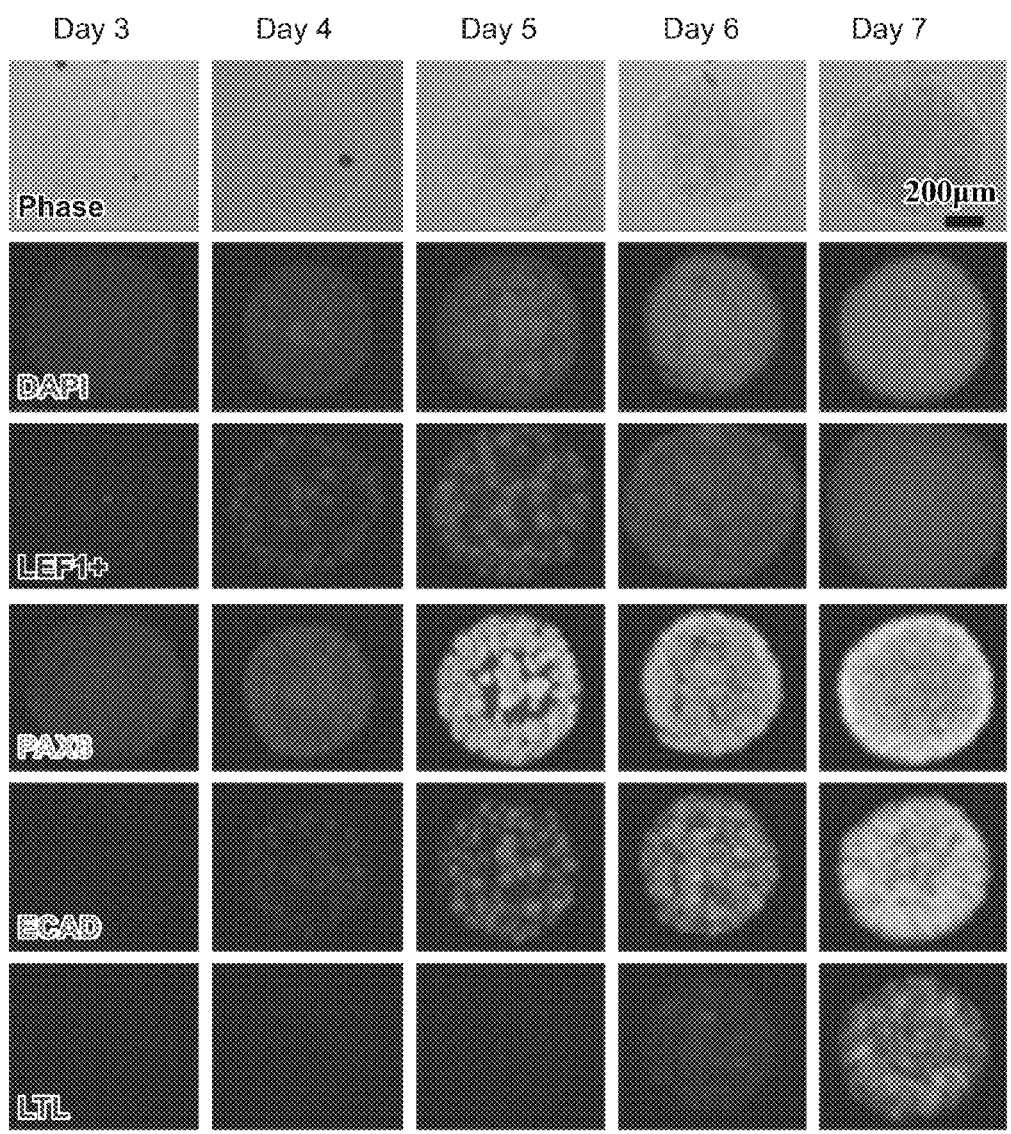

To confirm that in vitro propagated nephron progenitor cells retained their competence for nephron differentiation, their capacity for epithelial induction was tested under organotypic conditions in aggregate cultures containing a high concentration of CHIR (3 μM). Extensive tubulogenesis was seen in cells from passages 0, 1, and 2, but cells from passage 3 did not show any tubulogenesis (FIG. 8B). Aggregates of expanded progenitors cultured in differentiation conditions for 7 days revealed a molecular marker expression profile characteristic of proximal tubule differentiation (FIG. 8C). This included the sequential expression of LEF1 (PTA), ECAD (epithelialization), PAX8 (Comma and S-shaped body) and lotus lectin staining (mature proximal tubules).

Figure 8D:
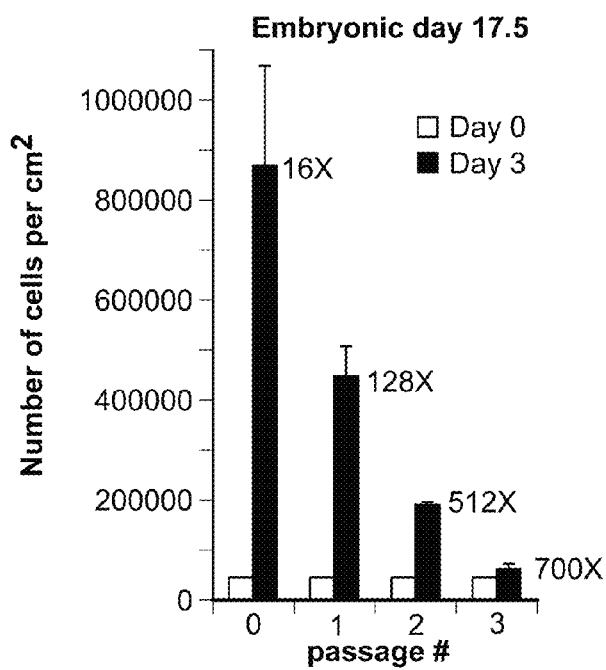
Figure 8E:
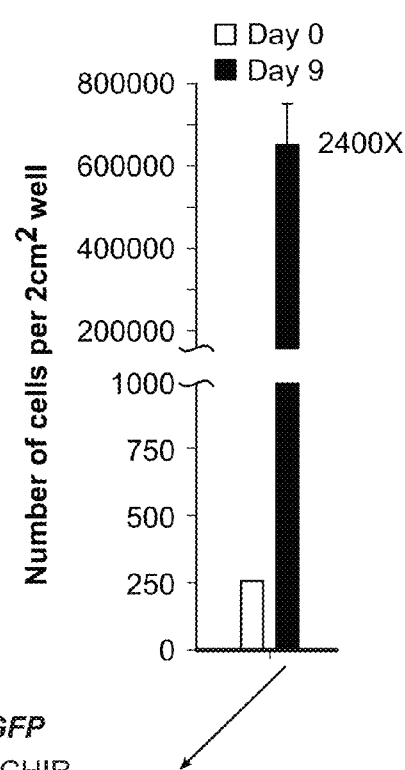
Figure 8F:
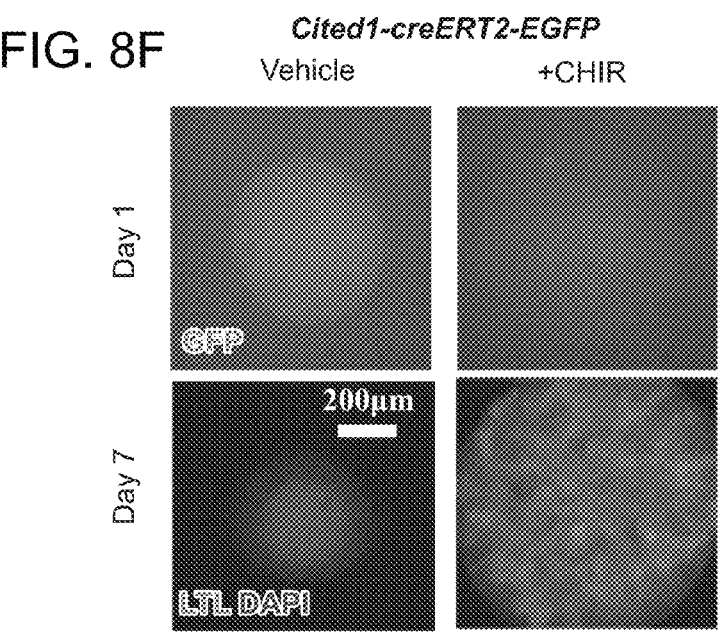

During the primary seeding at a density of 50,000 cells per cm$^2$ (FIG. 8A), it was identified that progenitors doubled 4 times in the first 3 days, resulting in a 16-fold expansion (FIG. 8D). However, each successive passage resulted in a net loss of one doubling such that at the end of passage 2 (9 days), the bulk culture of CITED1+ progenitors had doubled 9 times leading to a 512-fold expansion. However, cells plated at a lower density (250 cells per cm$^2$) and cultured without passage doubled approximately 11 times over a 9 day period leading to a 2,400-fold expansion, at which time they reached confluence (FIG. 8E). These cells expressed Cited1-driven GFP and also retained the capacity to differentiate into proximal tubules when placed into aggregate culture (FIG. 8F). Thus, cell passaging of high density cultures appeared to diminish both expansion and differentiation capacity, indicating that low density seeding of the primary isolate of cells yielded the most functionally robust cultures. The increased doubling time of low density seeded cultures could have been due to an outgrowth of progenitors with a selective advantage for expansion that was diminished in higher density culture and suggested the presence of heterogeneity in the CITED1+ compartment in vivo.

Figures 9B, 9C, 9D:
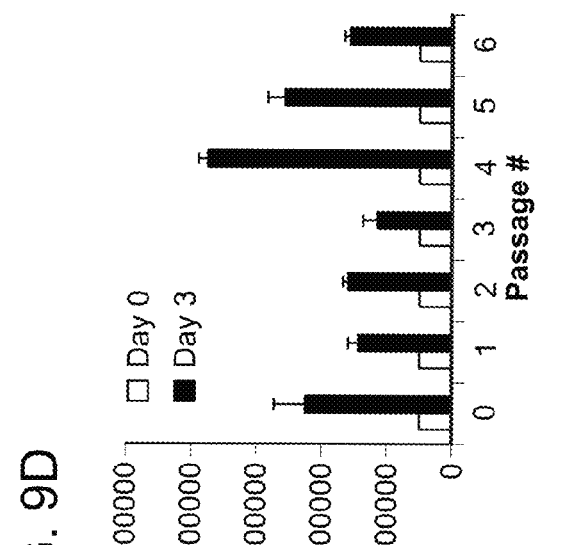
Figures 9E, 9F:
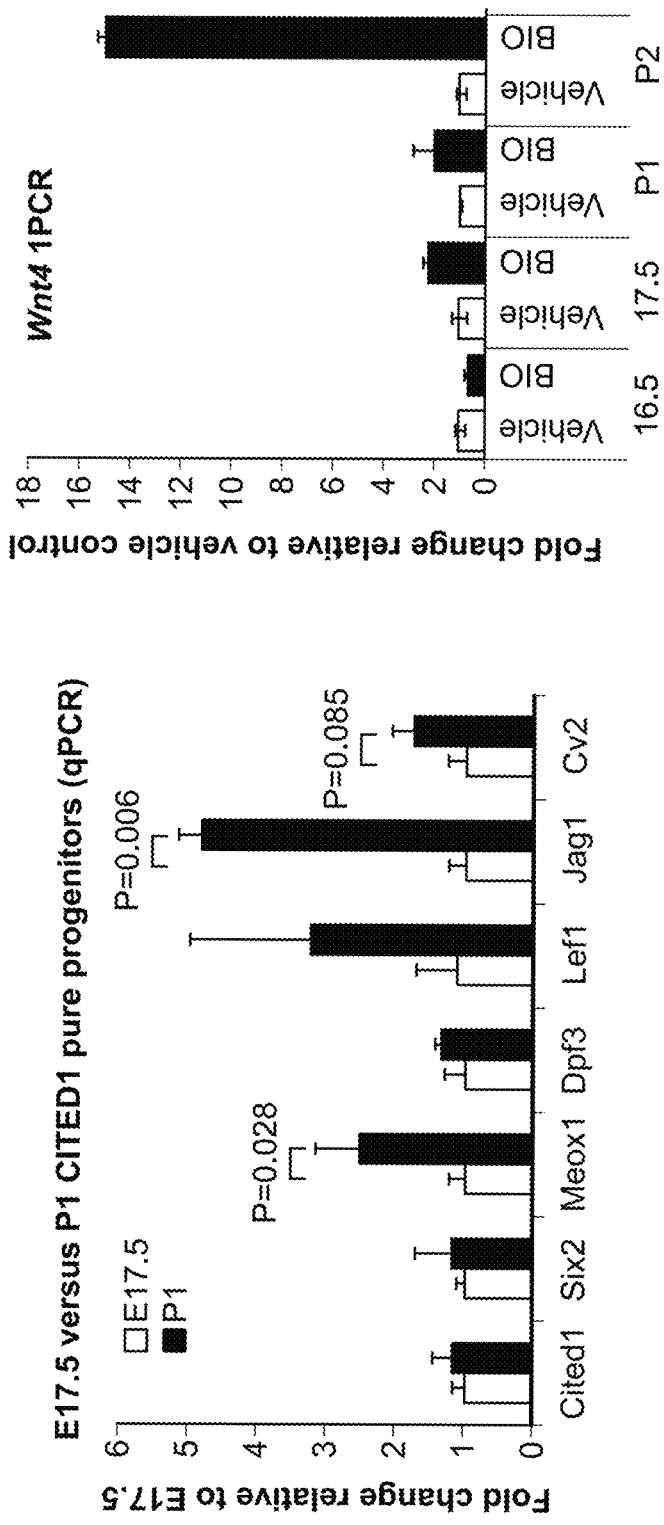

The majority of nephrons in the mouse kidney form after birth, and nephrogenesis begins to cease when the cap mesenchyme undergoes a final wave of differentiation and becomes depleted by P4 (Hartman et al., 2007). The cap mesenchyme undergoes a distinct phase of CITED1+ depletion between P1 and P2 (FIG. 6B) (Hartman et al., 2007). Because a decrease in proliferation of nephron progenitors and a continuous thinning of the cap occurs throughout nephrogenesis (Short et al., 2014), it was examined if CITED1+ progenitors isolated at P1 possessed only a limited capacity for expansion caused by mechanisms underlying cessation of nephrogenesis. To test this possibility, P1 CITED1+ progenitors were isolated (FIGS. 7A and 7B), cultured in NPEM, and monitored for expression by immunostaining. For each passage, P1 CITED1+ progenitors were seeded at a constant starting density (50,000 cells/cm$^2$) and, surprisingly, maintained robust CITED1 and SIX2 expression through 6 passages (FIG. 9A). In contrast to E17.5 progenitors, CITED1+ purity dropped slightly during each expansion period, but still remained greater than 90% after 5 passages (FIG. 9B). Robust differentiation was observed in aggregate cultures from each passage, even when CITED1+ purity had dropped to 65% at the end of passage 6 (FIGS. 9B and 9C). Initial proliferation of the fresh isolate (passage 0) was 4-fold lower for bulk P1 progenitors compared to those isolated at E17.5 (FIG. 8D and FIG. 9D). An interesting increase in proliferation occurred after passage 3, which subsided by passage 6. Overall, P1 progenitors doubled 12.5 times over 6 passages, resulting in approximately 6,000-fold expansion, taking into account the drop in CITED1+ purity. Previous marker analysis had shown that the CITED1+ compartment contained sub-domains that displayed heterogeneity in gene expression (Mugford et al., 2009). Meox1 and Dpf3 marked a subset of CITED1+ progenitors that were physically adjacent to the differentiating CITED1−/SIX2+ population, and it was therefore postulated that these markers may have identified a population of CITED1+ cells poised to differentiate. Gene expression data from freshly isolated CITED1+ progenitors indicated that P1 progenitors expressed equivalent levels of Cited1 and Six2, but higher levels of Meox1 compared to E17.5, suggesting that they may have begun to shift into a more differentiated CITED1+ subcompartment (FIG. 9E). P1 progenitors also displayed a statistically significant increase in expression of the marker Jag1, which normally displayed regionalized expression in the renal vesicle. Interestingly, JAG1 protein cycled during passaging, suggesting that it may also have played a role in undifferentiated progenitors (FIG. 9A). Consistent with increased pSMAD1/5 signaling in the more medullary cap mesenchyme at P1 (FIG. 6C), a slight trend was observed towards increased Cv2 gene expression (FIG. 9E). This increase in BMP-SMAD signaling would have been predicted to cause increased sensitivity of CITED1+ cells to WNT-β-catenin mediated differentiation (Brown et al., 2013). However, a functional test for differentiation that involved measuring Wnt4 expression in monolayer culture revealed that freshly isolated progenitors were not hypersensitive to a high concentration of BIO in the absence of additional BMP ligand, as was found for the progenitor isolate at P2, which indicated that P1 CITED1+ progenitors were not yet primed for differentiation by BMP signaling (FIG. 9E and Brown et al., 2013). Thus, P1 progenitors displayed a molecular marker signature consistent with increased differentiation within the CITED1+ compartment, but also possessed a greater potential to expand in bulk culture than E17.5 progenitors.

Example 4

SMAD Inhibition was Critical to Maintain Nephron Progenitor Potential

Figure 10A:
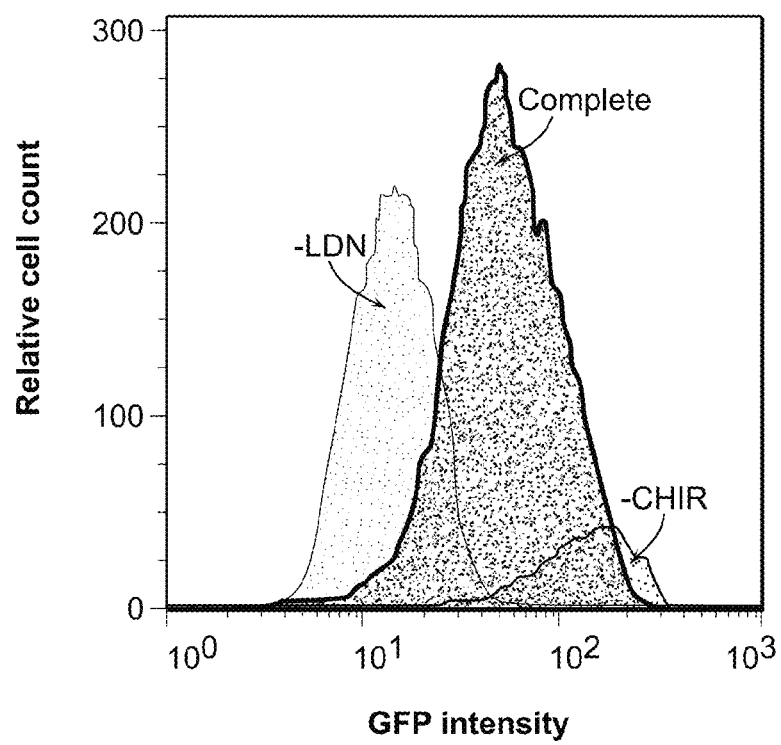
FIGS. 10A to 10F show that SMAD inhibition maintained nephron progenitor potential.
Figure 10B:
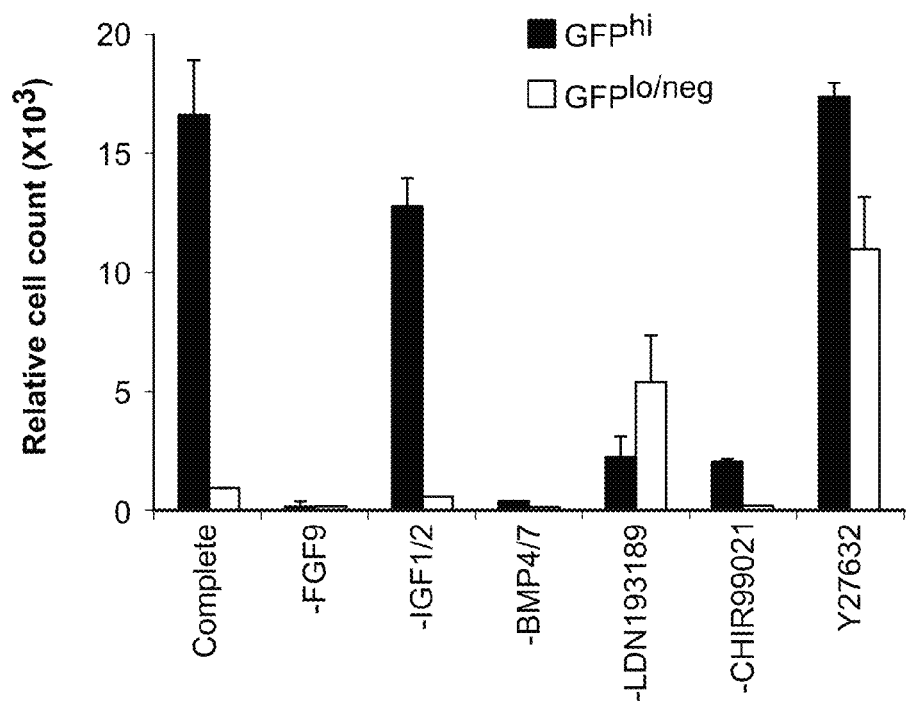
Figure 13A:
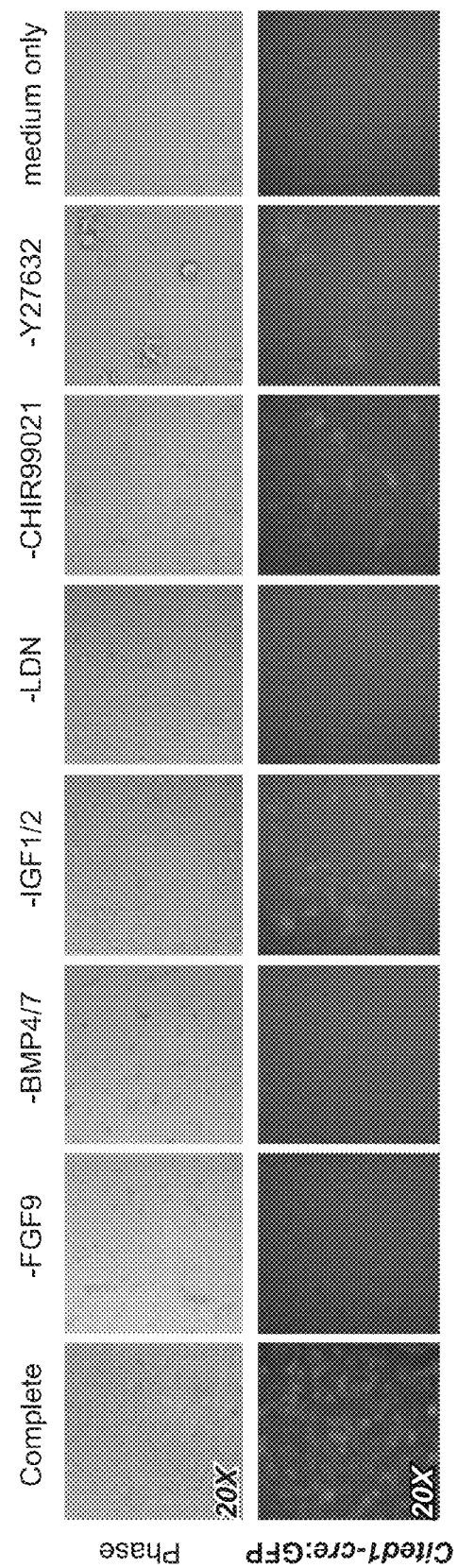
FIGS. 13A and 13B show growth of nephron progenitor cultures in the absence of individual factors.

Using flow cytometry on E17.5 CITED1+ progenitors derived from Cited1creERT2-EGFP mice, the requirement for each of the culture additives to maintain cells in the undifferentiated state was evaluated by subtracting them from the medium (FIGS. 10A and 10B). Progenitors grown in the absence of either FGF9 or BMP4/7 for 3 days failed to expand and displayed a shrunken morphology (FIG. 10B and FIG. 13A). Cells grown in the absence of IGF1/2 maintained CITED1 expression but grew more slowly than in the complete NPEM. In the absence of the WNT agonist CHIR, cells failed to expand but remained CITED1+ and looked morphologically similar to cells grown in complete NPEM (FIG. 10B and FIG. 13A). In the absence of the Rho kinase inhibitor Y-27632 there was a significant decrease in cell attachment, a corresponding increase in cell-cell contact, and importantly, a large proportion of progenitors unexpectedly transitioned out of the CITED1 compartment (FIG. 10B and FIG. 13A), which demonstrated that inhibition of this pathway played an important role in maintaining progenitor identity.

Figure 10C:
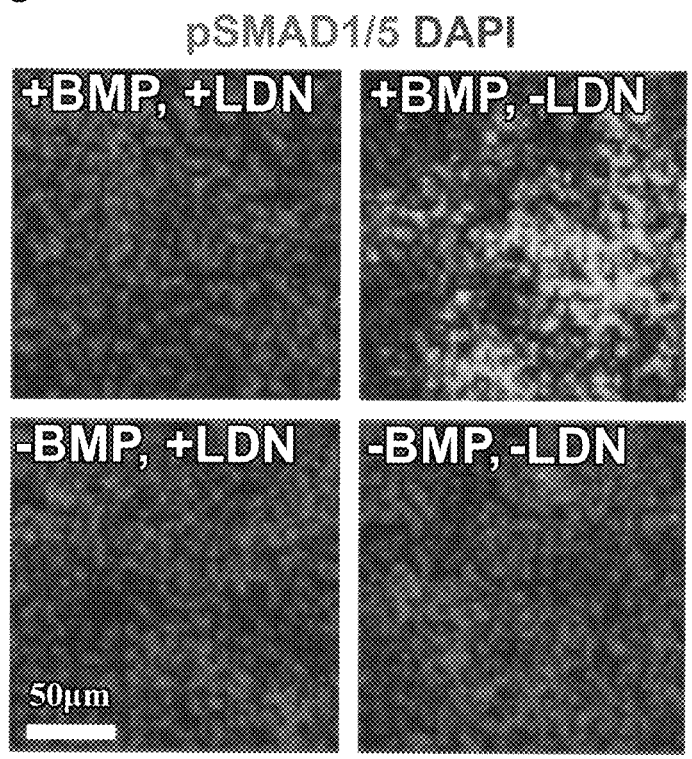
Figure 10D:
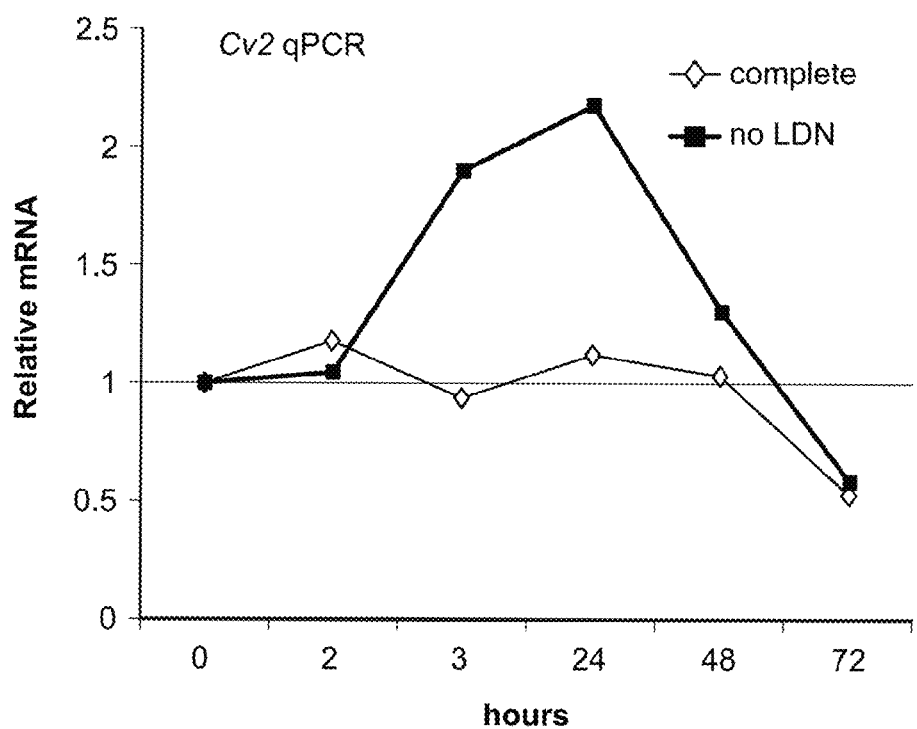
Figure 10E:
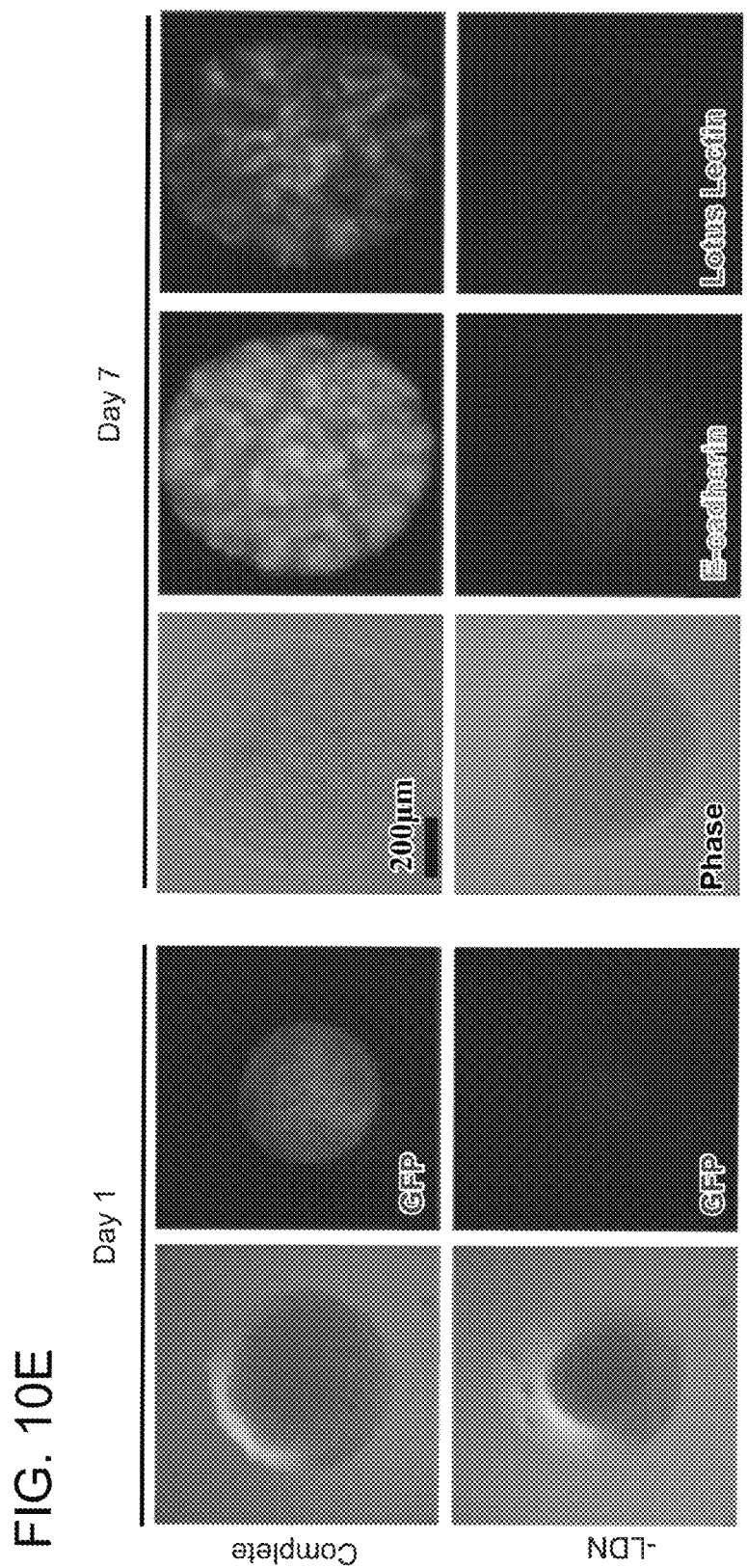
Figure 10F:
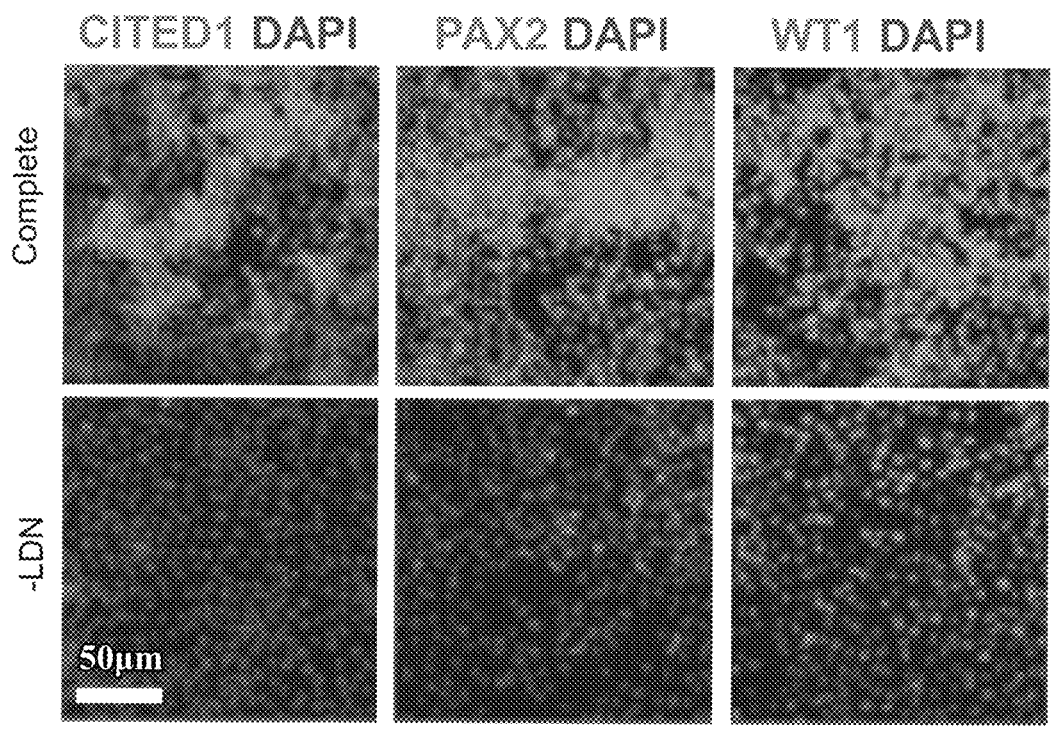
Figure 13B:
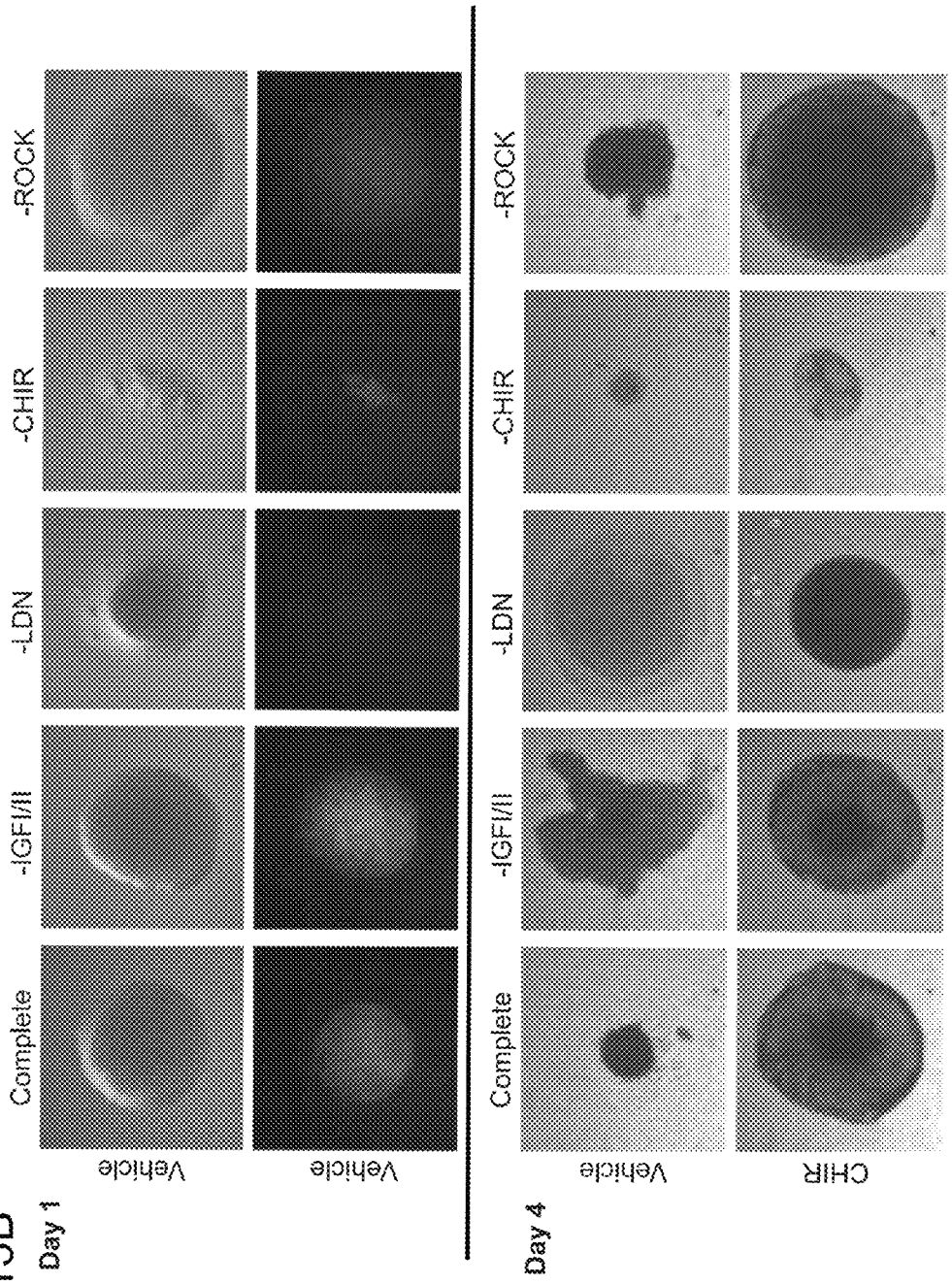
Figure 14:
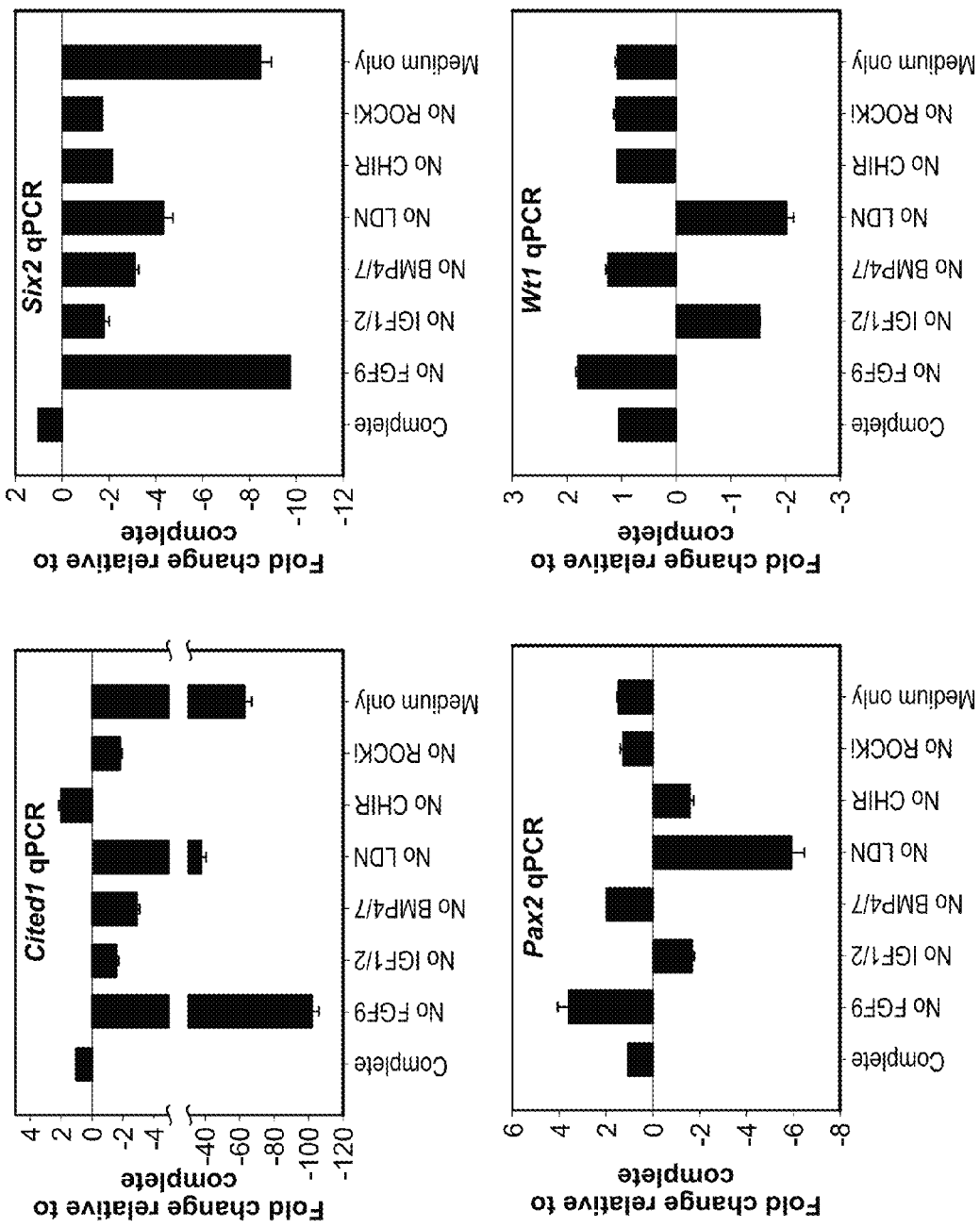
FIG. 14 shows nephron progenitor marker expression in cultures grown in the absence of individual factors. Purified CITED1 progenitors were grown in NPEM in the absence of individual factors for 3 days in monolayer culture. Cells were lysed and gene expression was measured by quantitative PCR. Fold changes were relative to cells grown in complete NPEM for each primer set. Results shown represent 3 pooled culture replicates derived from 20-24 pooled embryonic kidneys.
Figure 15A:
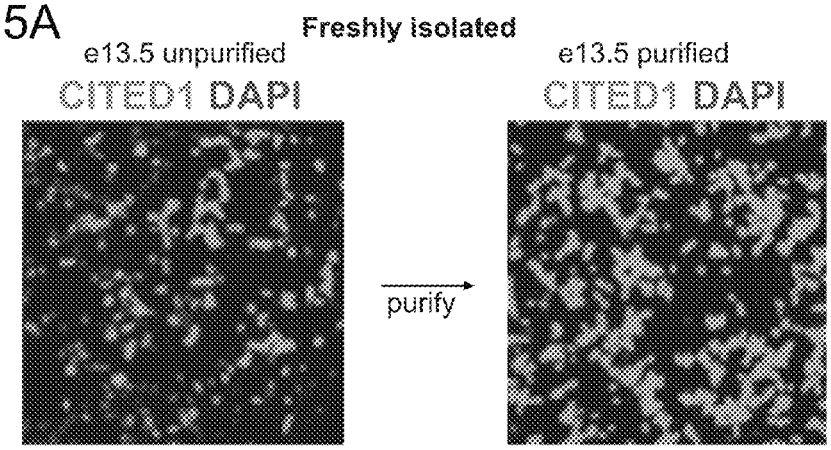
FIGS. 15A to 15C show that LDN was required to maintain CITED1+ progenitors derived from E13.5 embryonic kidneys.
Figure 15B:
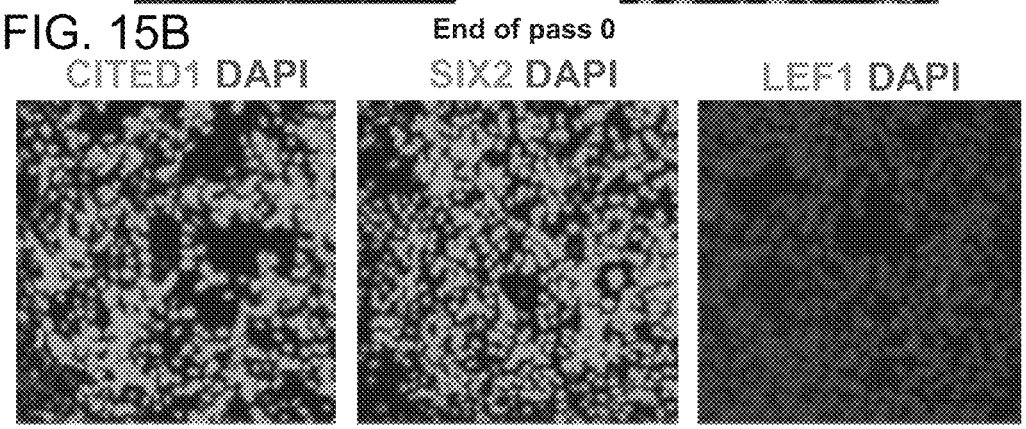
Figure 15C:
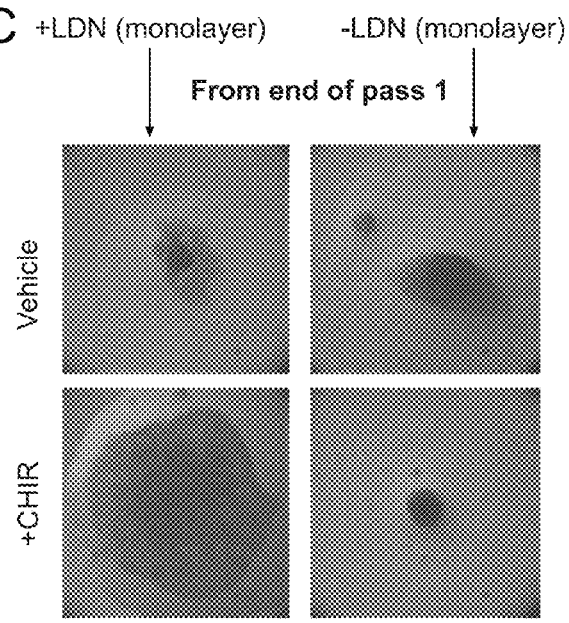

When LDN was subtracted from the medium, cells expanded but were largely CITED1 negative (FIGS. 10A and 10B). In the absence of LDN, nuclear localization of pSMAD1/5 increased dramatically, as did transcription of the SMAD response gene Cv2 (FIGS. 10C and 10D). While progenitors were still competent to undergo tubulogenesis after subtraction of IGF1/2, Y-27632 or CHIR, the absence of LDN rendered cells unable to undergo differentiation after 7 days in aggregate culture (FIG. 10E and FIG. 13B). In addition to losing CITED1 expression, progenitors cultured in the absence of LDN lost expression of characteristic marker genes including SIX2, PAX2, WT1 and SIX2, which may have helped to explain their lack of competence (FIG. 10F and FIG. 14). CITED1+ progenitors isolated from E13.5 kidneys also required LDN to expand while maintaining their competence to differentiate (FIG. 15). These results demonstrated that the SMAD signaling branch of the BMP pathway needed to be quenched to maintain nephron progenitor potential.

Example 5

Clonally Expanded Nephron Progenitors were Competent to Form Nephron Tubules

Figure 11A:
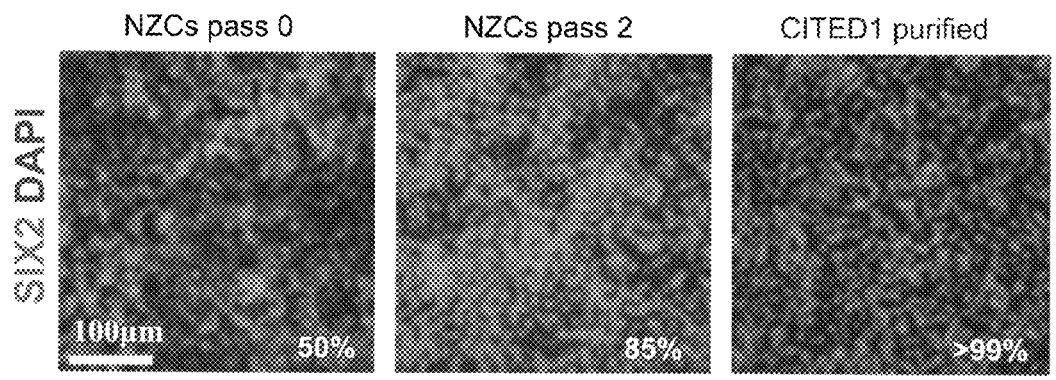
Figure 11B:
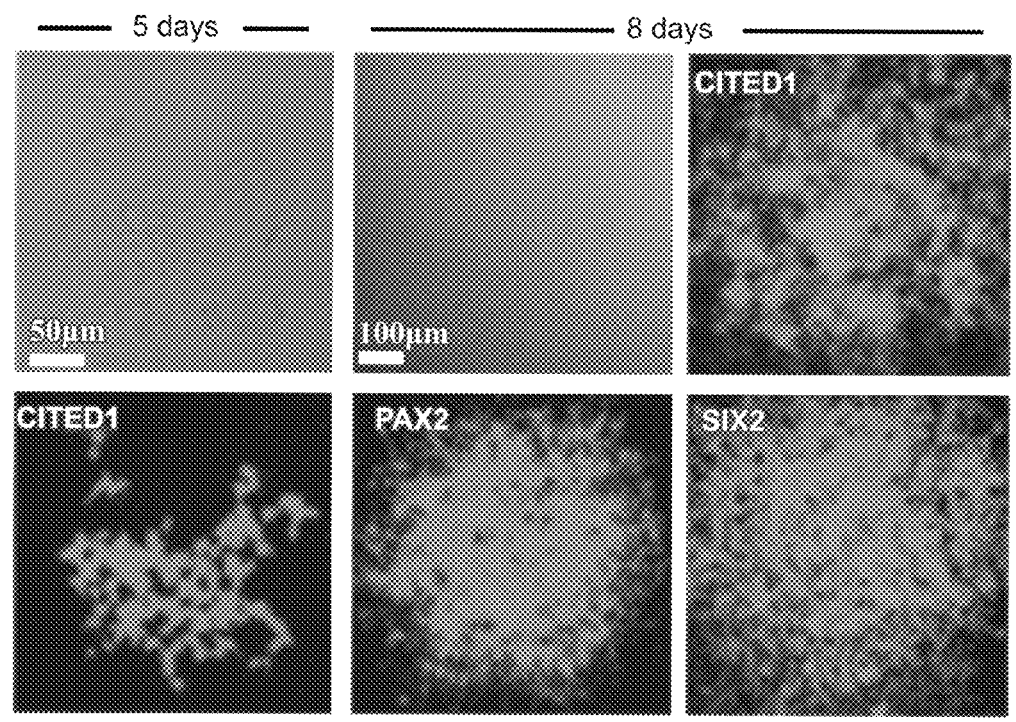

Thus, it was demonstrated above that bulk populations of pure CITED1+ progenitors could be expanded in NPEM while retaining their potential to undergo differentiation. Next, a mixed culture of cells isolated from the nephrogenic zone was tested to determine if the instant culture conditions conferred a selective growth advantage to nephron progenitor cells. An isolation method was used that resulted in a mixed population of approximately 50% nephron progenitor cells, 35% cortical interstitial cells and 15% other cells with trace contamination of collecting duct cells (Blank et al., 2009; Brown et al., 2011b; Brown et al., 2013). Expansion of a bulk culture of these nephrogenic zone cells (NZCs) increased the proportion of SIX2+ cells from 50% to 85% after 2 passages (FIG. 11A). Clones of CITED1+ cells expanded after 5 days in a limiting dilution assay using NZCs (FIG. 11B). Twenty independent clones were expanded for 8 days and all tested positive for CITED1, SIX2 or PAX2, indicating preferential outgrowth of cells of the nephron progenitor lineage (FIG. 11B). It was concluded that nephron progenitors expanded preferentially in NPEM over other cell types found within the nephrogenic zone and that nephron progenitor specific clones could be expanded from a single cell using the instant culture conditions.

Figure 16:
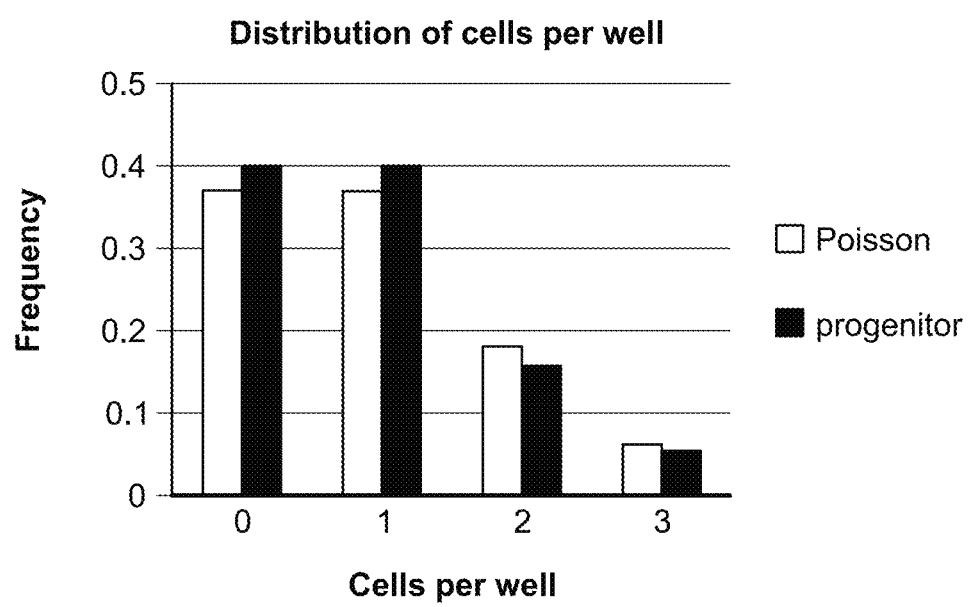
FIG. 16 shows the expected and observed Poisson distribution of a limiting dilution assay. A random sampling of 192 wells was chosen for the analysis and screened by light microscopy.
Figure 17B:
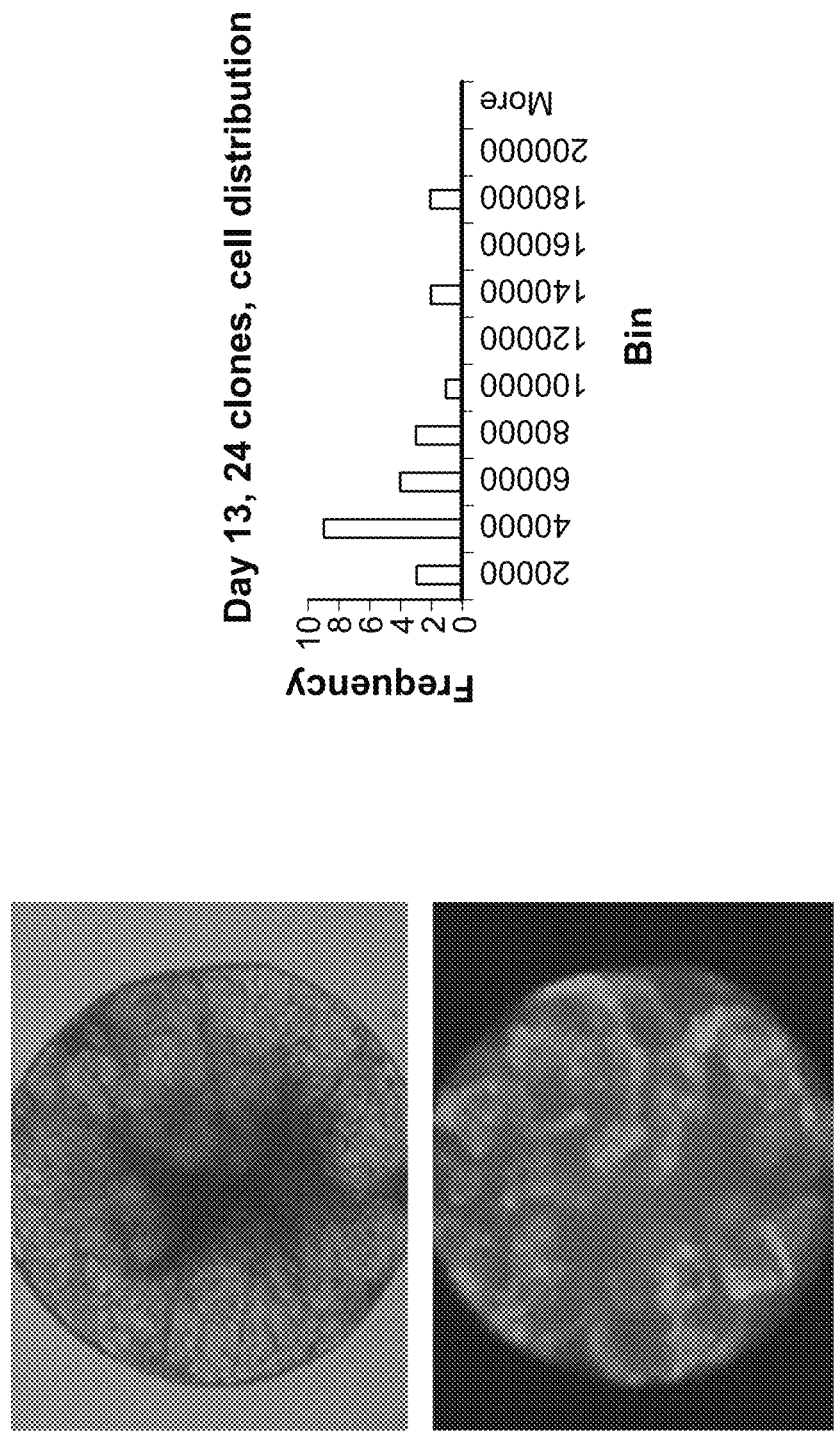

High density bulk cultures of E17.5 CITED1+ progenitors possessed limited capacity to expand. Heterogeneity of gene expression indicated that the CITED1+ compartment contained cells with varying degrees of progenitor potential (Mugford et al., 2009). To determine if the CITED1+ compartment represented a homo- or heterogeneous progenitor population, a limiting dilution analysis was performed. A total of 960 cells from a bulk population of CITED1+ progenitors purified from E17.5 kidneys, were distributed across ten 96 well plates. After attachment, the number of cells seeded per well mirrored the expected Poisson distribution (FIG. 16). After 5 days, many colonies had formed and the number of cells per clone was counted to compare the doubling times of individual progenitors (FIG. 11C). The growth rate observed was heterogeneous with 10% of clones doubling 7 times (17 hours per average doubling), a rate higher than that seen with our earlier low density seeding of bulk cultures (19.6 hours per average doubling). Wells containing a single colony derived from a single cell that fell within this higher proliferating category were interrogated further to determine their capacity for expansion. On day 12, 8 clones with an average cell count of 32,000 (15 doublings) were placed in aggregate culture and tested for their ability to differentiate (FIG. 17A). All 8 clones formed lotus lectin positive tubules, as seen with the bulk culture studies. This demonstrated that clonally derived progenitors remained competent to differentiate after 15 doublings.

Figure 11F:
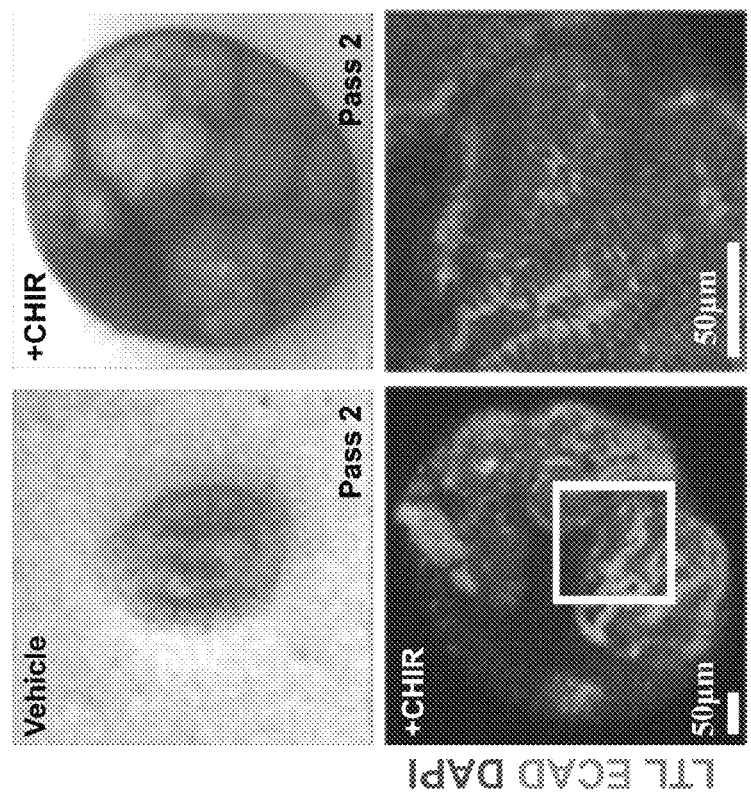
Figure 11E:
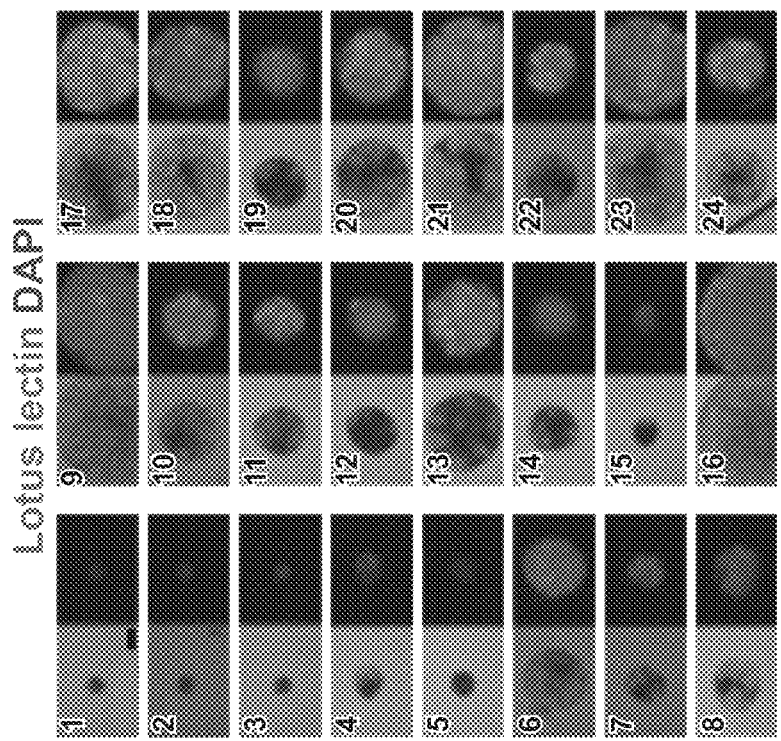

Many of the larger colonies were identified as having started to show increased clustering of cells, which could subject individual progenitors to non-uniform culture conditions, restrict growth potential or even cause spontaneous differentiation through increased cell-cell contact. To circumvent this and to expand the clones further, whether colonies could be dissociated and re-plated at a lower density in monolayer was tested. A test clone was passed at day 11 to a new well, spread uniformly and expanded to 128,800 cells (17 doublings) after 2 more days in monolayer. When this clone was transferred to aggregate culture, it underwent robust tubulogenesis under differentiating conditions (FIG. 17B), demonstrating that passage of clonally derived progenitors was possible and could extend their functional utility. In the same manner, 24 more high growth clones were split and passed to two wells each, expanded to confluence and either transferred to aggregate culture for differentiation or immunostained with anti-CITED1 antibody to determine purity. FIG. 11D shows the total number of cells expanded from each starting progenitor and the percent of cells that were CITED1+ within each clone. Over half of the clones were greater than 90% CITED1+ and 15 grew to more than 100,000 cells. There was a correlation between CITED1 purity and total cell expansion, with the 12 most expanded clones averaging 90% CITED1 purity and the 12 least expanding clones averaging only 60% purity. Several outlier clones (2, 7 and 17) had a lower cell number after the passage and when these cells were placed in aggregate culture, they had a reduced ability to undergo tubulogenesis, as compared to clones that were still expanding after the passage, indicating that they might have become compromised (FIG. 11E). Of the 24 clones, only 1 did not undergo tubulogenesis (#4), and this clone was associated with the lowest percentage of CITED1+ progenitors (4%). The remaining 23 clones underwent partial to complete tubulogenesis when subjected to differentiating conditions in aggregate culture. One healthy clone was further expanded over a period of 23 days including 2 passages and underwent extensive tubulogenesis when transferred to aggregate (FIG. 11F). Confocal microscopy of this clonally derived aggregate showed numerous E-cadherin and lotus lectin positive tubules with lumens that could be visualized by optical sectioning. Overall, these results provided the first functional evidence that the CITED1+ compartment is comprised of nephron progenitor cells that display a wide variability in progenitor potential.

Example 6

Expansion of Functional Nephron Progenitor Cells Derived from hESCs

Figure 18A:
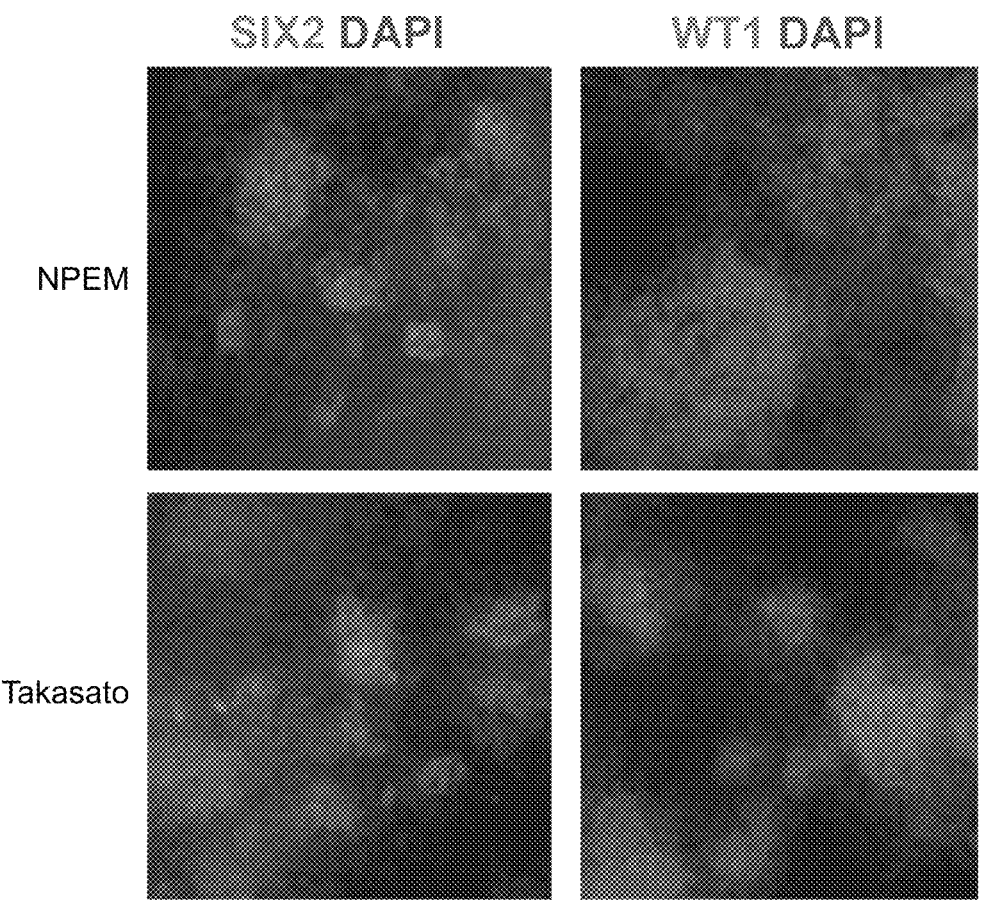
FIGS. 18A and 18B show SIX2 and WT1 expression in human nephron progenitors derived from human ES cells after pass 0 and 2.
Figure 18B:
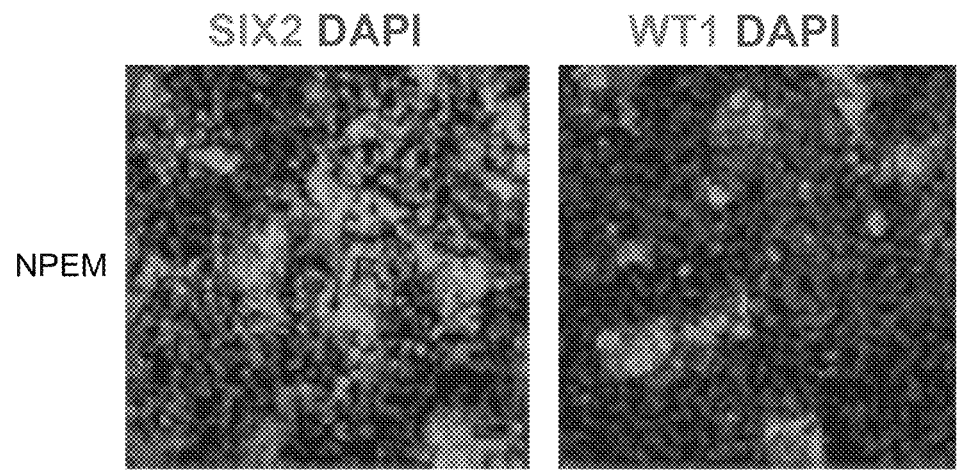
Figure 19A:
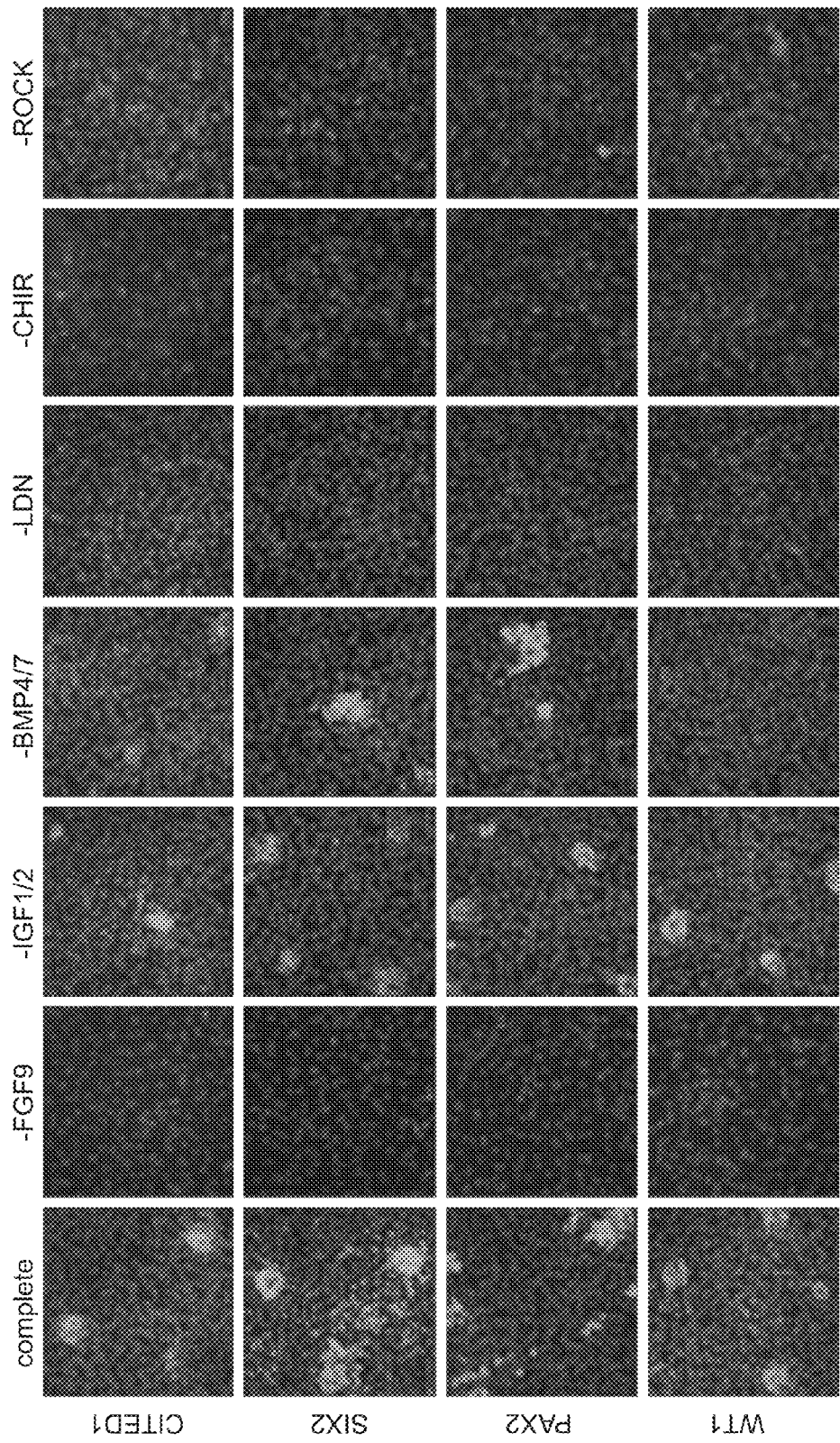
FIGS. 19A and 19B show nephron progenitor marker expression in human ES cell derived cultures grown in the absence of individual factors.
Figure 19B:
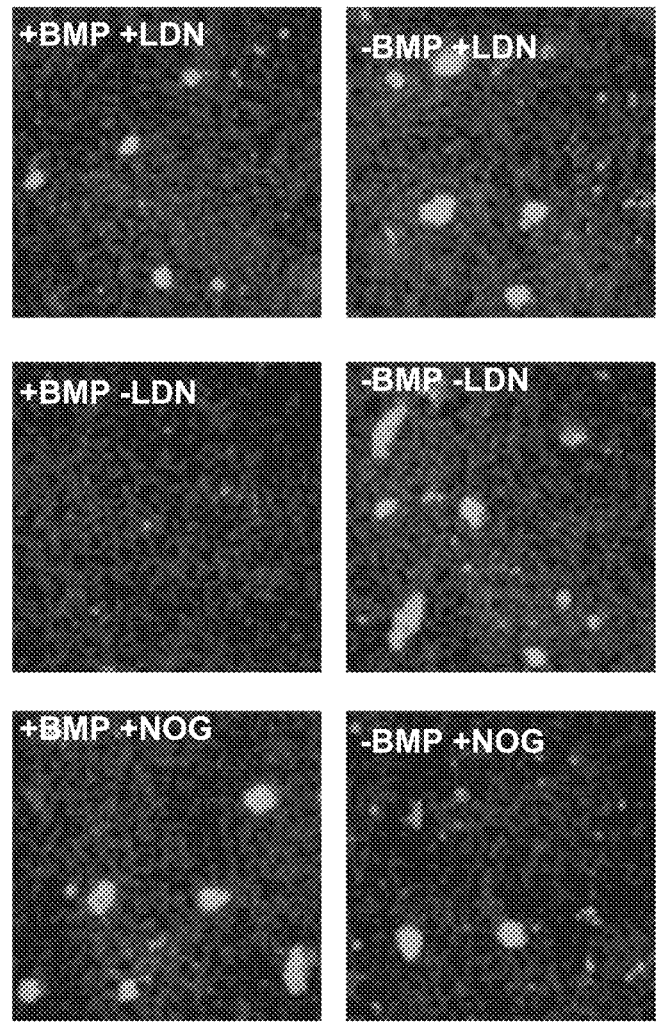

To understand if cellular growth in NPEM could be directly extrapolated to human cells, the above analysis was repeated with nephron progenitor cells derived from hESCs using the Takasato protocol (Takasato et al., 2014). CITED1+/SIX2+/PAX2+/WT1+ cells generated using this procedure lost expression of nephron progenitor markers following a single passage (FIG. 12A and FIG. 18A). However, hESC-derived nephron progenitors could be passaged at least twice (1:8 split) with retained molecular marker expression using our propagation conditions (FIG. 12B and FIG. 18B). Subtraction of individual components from the medium revealed a critical dependence on FGF9, LDN, CHIR and Y27632 for expression of CITED1, PAX2, SIX2 and WT1 (FIG. 19A). When LDN was eliminated from the medium during the passage 2 culture, cells lost expression of PAX2 (FIG. 12C). When BMP4/7 was removed, PAX2 and SIX2 expression remained robust, whereas CITED1 was decreased and WT1 was eliminated (FIG. 19A). Interestingly, when both BMP4/7 and LDN were removed concurrently, PAX2 expression remained, indicating that LDN might only have been necessary to retain marker expression in the presence of exogenous BMP (FIG. 19B).

Figure 12F:
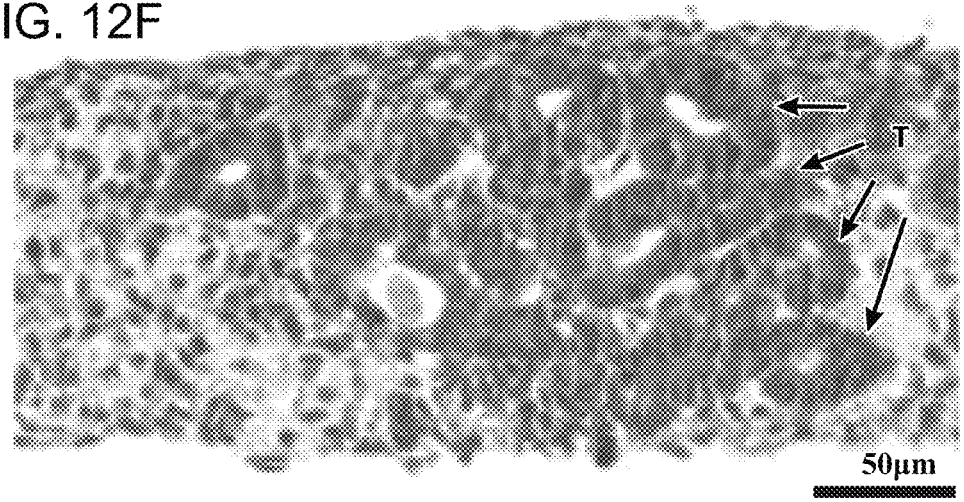
Figure 12G:
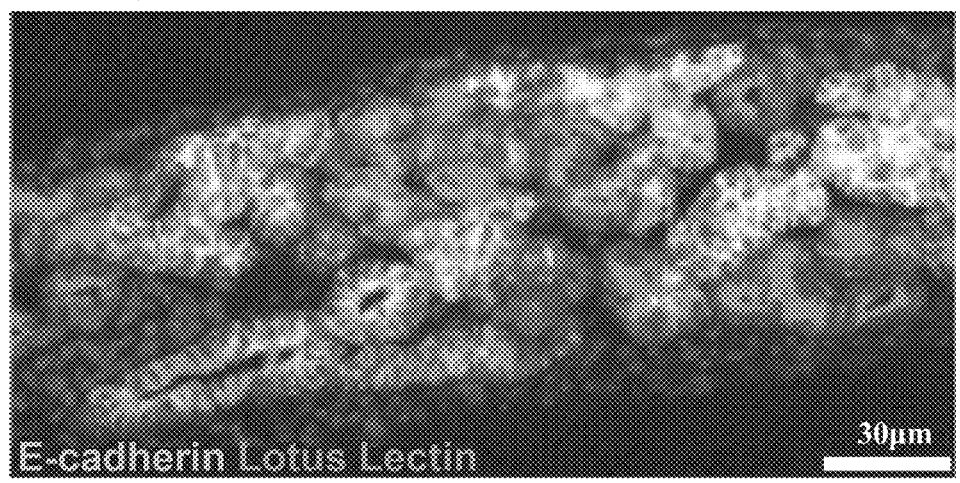
Figure 12H:
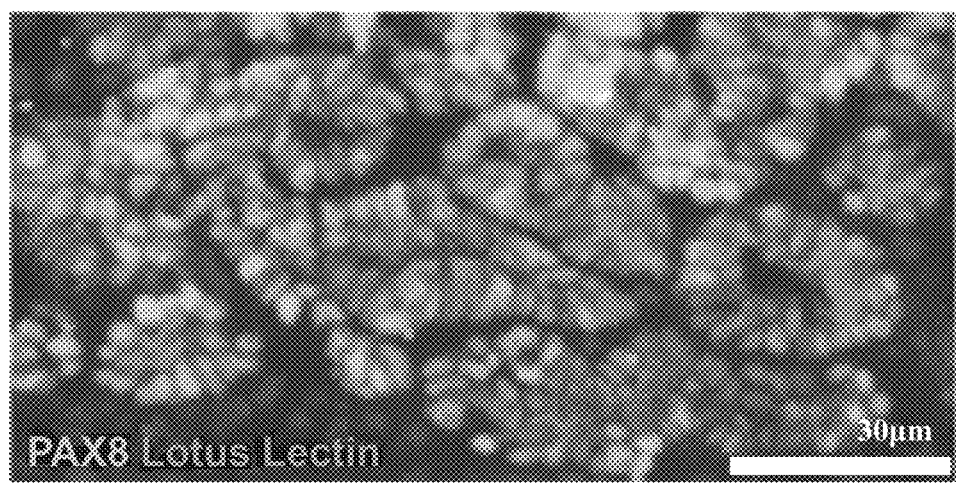

To evaluate the functional capacity of expanded human nephron progenitor cells, cell aggregates from each passage were differentiated. Very few tubules formed from cells expanded during passages 0 and 1 in either medium, although the tubules that did form stained positive for lotus lectin (FIG. 12E). In contrast, cells cultured through passage 2 in NPEM underwent robust differentiation forming many tubules containing lumens (FIGS. 12E and 12F). Staining for both E-cadherin and lotus lectin were identified in differentiated tubules, and it was observed that tubules frequently expressed both of these markers (FIG. 12G). When found in tubules without E-cadherin, lotus lectin staining was confined to the luminal side of tubules, where it normally stained L-fucose present on the surface of the microvilli that form the brush border. This indicated that these tubules possessed increased surface area, which was necessary for the resorptive and flow-sensing functions of proximal tubules in vivo. Persistent nuclear expression of PAX8 was also observed—PAX8 is normally expressed in proximal and distal convoluted tubules and loops of Henle in humans, but was identified as decreased or absent in adult mouse kidneys (FIG. 12H and Tong et al., 2009). PAX8 staining also showed alternating expression intensity in neighboring cells within a tubular structure, similar to that observed in human proximal tubules (Tong et al., 2009). In tubules co-expressing both markers, lotus lectin often overlapped with E-cadherin staining at cell-cell junctions, but displayed stronger expression towards the luminal side (FIG. 12G). Without wishing to be bound by theory, since this pattern was only found in E-cadherin positive tubules, and E-cadherin expression is normally decreased prior to terminal differentiation of the proximal tubule in mice and rats (Prozialeck et al., 2004), these structures may represent immature tubules where microvilli have not yet formed and in which expression of these two markers has not yet segregated. Another possibility is that the immediate precursors to proximal and distal tubule epithelial cells (LTL−/ECAD+) have become intermixed and given rise to a number of hybrid tubules within the organoid culture, rather than becoming regionally restricted to a single tubule type. Overall, it was demonstrated that NPEM expanded ES cell-derived human nephron progenitors that were capable of robust epithelialization and formation of tubules with lumens that displayed expression of markers normally associated with human proximal tubules.

REFERENCES

Abdel-Kader, K., Unruh, M. L., and Weisbord, S. D. (2009). Symptom burden, depression, and quality of life in chronic and end-stage kidney disease. Clinical journal of the American Society of Nephrology: CJASN 4, 1057-1064.

Bach, L. A., and Hale, L. J. (2014). Insulin-like Growth Factors and Kidney Disease. American journal of kidney diseases: the official journal of the National Kidney Foundation.

Barak, H., Huh, S. H., Chen, S., Jeanpierre, C., Martinovic, J., Parisot, M., Bole-Feysot, C., Nitschke, P., Salomon, R., Antignac, C., et al. (2012). FGF9 and FGF20 Maintain the Stemness of Nephron Progenitors in Mice and Man. Dev Cell 22, 1191-1207.

Blank, U., Brown, A., Adams, D. C., Karolak, M. J., and Oxburgh, L. (2009). BMP7 promotes proliferation of nephron progenitor cells via a JNK-dependent mechanism. Development 136, 3557-3566.

Boyle, S., Misfeldt, A., Chandler, K. J., Deal, K. K., Southard-Smith, E. M., Mortlock, D. P., Baldwin, H. S., and de Caestecker, M. (2008a). Fate mapping using Cited1-CreERT2 mice demonstrates that the cap mesenchyme contains self-renewing progenitor cells and gives rise exclusively to nephronic epithelia. Dev Biol 313, 234-245.

Boyle, S., Misfeldt, A., Chandler, K. J., Deal, K. K., Southard-Smith, E. M., Mortlock, D. P., Baldwin, H. S., and de Caestecker, M. (2008b). Fate mapping using Cited1-CreERT2 mice demonstrates that the cap mesenchyme contains self-renewing progenitor cells and gives rise exclusively to nephronic epithelia. Developmental biology 313, 234-245.

Brown, A. C., Adams, D., de Caestecker, M., Yang, X., Friesel, R., and Oxburgh, L. (2011a). FGF/EGF signaling regulates the renewal of early nephron progenitors during embryonic development. Development 138, 5099-5112.

Brown, A. C., Blank, U., Adams, D. C., Karolak, M. J., Fetting, J. L., Hill, B. L., and Oxburgh, L. (2011b). Isolation and culture of cells from the nephrogenic zone of the embryonic mouse kidney. J Vis Exp.

Brown, A. C., Muthukrishnan, S. D., Guay, J. A., Adams, D. C., Schafer, D. A., Fetting, J. L., and Oxburgh, L. (2013). Role for compartmentalization in nephron progenitor differentiation. Proc Natl Acad Sci USA 110, 4640-4645.

Carroll, T. J., Park, J. S., Hayashi, S., Majumdar, A., and McMahon, A. P. (2005). Wnt9b plays a central role in the regulation of mesenchymal to epithelial transitions underlying organogenesis of the Mammalian urogenital system. Dev Cell 9, 283-292.

Das, A., Tanigawa, S., Karner, C. M., Xin, M., Lum, L., Chen, C., Olson, E. N., Perantoni, A. O., and Carroll, T. J. (2013). Stromal-epithelial crosstalk regulates kidney progenitor cell differentiation. Nat Cell Biol 15, 1035-1044.

Fetting, J. L., Guay, J. A., Karolak, M. J., Iozzo, R. V., Adams, D. C., Maridas, D. E., Brown, A. C., and Oxburgh, L. (2014). FOXD1 promotes nephron progenitor differentiation by repressing decorin in the embryonic kidney. Development 141, 17-27.

Hartman, H. A., Lai, H. L., and Patterson, L. T. (2007). Cessation of renal morphogenesis in mice. Dev Biol 310, 379-387.

Humphreys, B. D., Valerius, M. T., Kobayashi, A., Mugford, J. W., Soeung, S., Duffield, J. S., McMahon, A. P., and Bonventre, J. V. (2008). Intrinsic epithelial cells repair the kidney after injury. Cell stem cell 2, 284-291.

Karner, C. M., Das, A., Ma, Z., Self, M., Chen, C., Lum, L., Oliver, G., and Carroll, T. J. (2011). Canonical Wnt9b signaling balances progenitor cell expansion and differentiation during kidney development. Development 138, 1247-1257.

Kobayashi, A., Valerius, M. T., Mugford, J. W., Carroll, T. J., Self, M., Oliver, G., and McMahon, A. P. (2008). Six2 defines and regulates a multipotent self-renewing nephron progenitor population throughout mammalian kidney development. Cell stem cell 3, 169-181.

Lam, A. Q., Freedman, B. S., Morizane, R., Lerou, P. H., Valerius, M. T., and Bonventre, J. V. (2013). Rapid and Efficient Differentiation of Human Pluripotent Stem Cells into Intermediate Mesoderm That Forms Tubules Expressing Kidney Proximal Tubular Markers. Journal of the American Society of Nephrology: JASN.

Little, M. H., and Bertram, J. F. (2009). Is there such a thing as a renal stem cell? Journal of the American Society of Nephrology: JASN 20, 2112-2117.

Mae, S., Shono, A., Shiota, F., Yasuno, T., Kajiwara, M., Gotoda-Nishimura, N., Arai, S., Sato-Otubo, A., Toyoda, T., Takahashi, K., et al. (2013). Monitoring and robust induction of nephrogenic intermediate mesoderm from human pluripotent stem cells. Nature communications 4, 1367.

Mori, K., Yang, J., and Barasch, J. (2003). Ureteric bud controls multiple steps in the conversion of mesenchyme to epithelia. Seminars in cell & developmental biology 14, 209-216.

Motamedi, F. J., Badro, D. A., Clarkson, M., Rita Lecca, M., Bradford, S. T., Buske, F. A., Saar, K., Hubner, N., Brandli, A. W., and Schedl, A. (2014). WT1 controls antagonistic FGF and BMPpSMAD pathways in early renal progenitors. Nat Commun 5, 4444.

Mugford, J. W., Yu, J., Kobayashi, A., and McMahon, A. P. (2009). High-resolution gene expression analysis of the developing mouse kidney defines novel cellular compartments within the nephron progenitor population. Dev Biol 333, 312-323.

Osafune, K., Takasato, M., Kispert, A., Asashima, M., and Nishinakamura, R. (2006). Identification of multipotent progenitors in the embryonic mouse kidney by a novel colonyforming assay. Development 133, 151-161.

Oxburgh, L., Dudley, A. T., Godin, R. E., Koonce, C. H., Islam, A., Anderson, D. C., Bikoff, E. K., and Robertson, E. J. (2005). BMP4 substitutes for loss of BMP7 during kidney development. Dev Biol 286, 637-646.

Park, J. S., Ma, W., O'Brien, L. L., Chung, E., Guo, J. J., Cheng, J. G., Valerius, M. T., McMahon, J. A., Wong, W. H., and McMahon, A. P. (2012). Six2 and Wnt regulate self-renewal and commitment of nephron progenitors through shared gene regulatory networks. Dev Cell 23, 637-651.

Prozialeck, W. C., Lamar, P. C., and Appelt, D. M. (2004). Differential expression of E-cadherin, N-cadherin and beta-catenin in proximal and distal segments of the rat nephron. BMC physiology 4, 10.

Rogers, S. A., Powell-Braxton, L., and Hammerman, M. R. (1999). Insulin-like growth factor I regulates renal development in rodents. Dev Genet 24, 293-298.

Self, M., Lagutin, O. V., Bowling, B., Hendrix, J., Cai, Y., Dressler, G. R., and Oliver, G. (2006). Six2 is required for suppression of nephrogenesis and progenitor renewal in the developing kidney. The EMBO journal 25, 5214-5228.

Short, K. M., Combes, A. N., Lefevre, J., Ju, A. L., Georgas, K. M., Lamberton, T., Cairncross, O., Rumballe, B. A., McMahon, A. P., Hamilton, N. A., et al. (2014). Global quantification of tissue dynamics in the developing mouse kidney. Dev Cell 29, 188-202.

Taguchi, A., Kaku, Y., Ohmori, T., Sharmin, S., Ogawa, M., Sasaki, H., and Nishinakamura, R. (2014). Redefining the in vivo origin of metanephric nephron progenitors enables generation of complex kidney structures from pluripotent stem cells. Cell Stem Cell 14, 53-67.

Takahashi, K., and Yamanaka, S. (2006). Induction of pluripotent stem cells from mouse embryonic and adult fibroblast cultures by defined factors. Cell 126, 663-676.

Takasato, M., Er, P. X., Becroft, M., Vanslambrouck, J. M., Stanley, E. G., Elefanty, A. G., and Little, M. H. (2014). Directing human embryonic stem cell differentiation towards a renal lineage generates a self-organizing kidney. Nat Cell Biol 16, 118-126.

Tong, G. X., Yu, W. M., Beaubier, N. T., Weeden, E. M., Hamele-Bena, D., Mansukhani, M. M., and O'Toole, K. M. (2009). Expression of PAX8 in normal and neoplastic renal tissues: an immunohistochemical study. Modern pathology: an official journal of the United States and Canadian Academy of Pathology, Inc 22, 1218-1227.

Tsutsui, H., Valamehr, B., Hindoyan, A., Qiao, R., Ding, X., Guo, S., Witte, O. N., Liu, X., Ho, C. M., and Wu, H. (2011). An optimized small molecule inhibitor cocktail supports long-term maintenance of human embryonic stem cells. Nature communications 2, 167.

Venkataraman, G., Sasisekharan, V., Herr, A. B., Ornitz, D. M., Waksman, G., Cooney, C. L., Langer, R., and Sasisekharan, R. (1996). Preferential self-association of basic fibroblast growth factor is stabilized by heparin during receptor dimerization and activation. Proc Natl Acad Sci U S A 93, 845-850.

Watanabe, K., Ueno, M., Kamiya, D., Nishiyama, A., Matsumura, M., Wataya, T., Takahashi, J. B., Nishikawa, S., Nishikawa, S., Muguruma, K., et al. (2007). A ROCK inhibitor permits survival of dissociated human embryonic stem cells. Nature biotechnology 25, 681-686.

Yu, P. B., Deng, D. Y., Lai, C. S., Hong, C. C., Cuny, G. D., Bouxsein, M. L., Hong, D. W., McManus, P. M., Katagiri, T., Sachidanandan, C., et al. (2008). BMP type I receptor inhibition reduces heterotopic [corrected] ossification. Nat Med 14, 1363-1369.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A composition for expanding a mammalian progenitor cell population comprising FGF9 at 25 to 250 ng/ml, LDN-193189 at 5 to 300 nM, CHIR 99021 at 100 to 10,000 nM and at least one of BMP7 and BMP4.

2. The composition of claim 1, wherein said mammalian progenitor cell population is a nephron progenitor cell population.

3. The composition of claim 1, further comprising ROCKi.

4. The composition of claim 1, further comprising at least one of IGF1, IGF2 and Heparin.

5. The composition of claim 1, further comprising one or more compositions selected from the group consisting of APEL or DMEM/F12+KOSR as media and matrigel or gelatin as ECM (extracellular matrix).

6. The composition of claim 1 comprising at least one component selected from the group consisting of:
   BMP7 (Bone morphogenetic protein 7, aka osteogenic protein-1 or OP-1) present at 5 to 100ng/ml;
   BMP4 (Bone morphogenetic protein 4) present at 5 to 100 ng/ml;
   ROCKi at 1 to 10 µM;
   IGF1 (Insulin-like growth factor 1, also called somatomedin C) present at 20 ng/ml; and
   IGF2 (Insulin-like growth factor 2) present at 2 ng/ml.

7. The composition of claim 6, comprising at least one component selected from the group consisting of:
   FGF9 (glia activating factor) present at 200 ng/ml;
   BMP7 (Bone morphogenetic protein 7, aka osteogenic protein-1 or OP-1) present at 30ng/ml;
   BMP4 (Bone morphogenetic protein 4) present at 30 ng/ml;
   LDN (BMP inhibitor LDN-193189) present at 75 nM; and
   CHIR 99021 present at 1 µM.

8. The composition of claim 1, comprising at least one component selected from the group consisting of IGF1 present at 5 to 100 ng/ml; IGF2 present at 0.1 to 10 ng/ml; and Heparin present at 1 to 10 µg/mg.

9. The composition of claim 1, comprising at least one component selected from the group consisting of IGF1 present at 20 ng/ml; IGF2 present at 2 ng/ml; Heparin present at 1 µg/mg; and ROCKi present at 10 µM.

10. A method for expanding a mammalian progenitor cell population comprising:
   a) obtaining a mammalian progenitor cell population;
   b) contacting said mammalian progenitor cell population with a composition of claim 1; and
   c) incubating said mammalian progenitor cell population with said composition for a time sufficient to allow for expansion of said mammalian progenitor cell population, thereby expanding said mammalian progenitor cell population.

11. The method of claim 10, wherein said mammalian progenitor cell population is a nephron progenitor cell population.

12. The method of claim 10, wherein said mammalian progenitor cell population is expanded by an amount selected from the group consisting of at least 10-fold, at least 100-fold, 256-fold, at least 1000-fold, 4096-fold and at least 5000-fold.

13. The method of claim 10, wherein said mammalian progenitor cell population is derived from embryonic stem cells.

14. The method of claim 10, wherein said mammalian progenitor cell population is human or murine.

15. The method of claim 10, wherein said incubating occurs for a duration of time selected from at least 18 hours, at least 2 days, at least 4 days and at least 9 days.

16. The method of claim 10, wherein said mammalian progenitor cell population has a doubling time of 18 hours.

17. The method of claim 10, wherein said cells are passaged every three days after four doublings.

18. A method for expanding a mammalian progenitor cell population within a mammalian stem cell population comprising:
   a) obtaining a mammalian stem cell population comprising mammalian progenitor cells;
   b) contacting said mammalian stem cell population with a composition of claim 1; and
   c) incubating said mammalian stem cell population with said composition for a time sufficient to allow for expansion of said mammalian progenitor cell population within said mammalian stem cell population, thereby expanding said mammalian progenitor cell population within said mammalian stem cell population.

19. The method of claim 18, wherein said mammalian progenitor cell population is a nephron progenitor cell population.

20. The method of claim 18, wherein said mammalian progenitor cell population is expanded by an amount selected from the group consisting of at least 2-fold, at least 5-fold, at least 10-fold and at least 20-fold.

21. The method of claim 18, wherein said mammalian progenitor cell population is initially present at less than 5% within said mammalian stem cell population.

22. The method of claim 18, wherein said mammalian progenitor cell population comprises at least 50% of all cells after incubating said mammalian stem cell population with said composition for a time sufficient to allow for expansion of said mammalian progenitor cell population within said mammalian stem cell population.

* * * * *

UNITED STATES PATENT AND TRADEMARK OFFICE
CERTIFICATE OF CORRECTION

Page 1 of 1

PATENT NO. : 9,752,115 B2
APPLICATION NO. : 14/632454
DATED : August 1, 2017
INVENTOR(S) : Leif Oxburgh et al.

It is certified that error appears in the above-identified patent and that said Letters Patent is hereby corrected as shown below:

In the Specification

Column 1, Lines 16-20, delete:
"Research supporting this application was carried out in part under funding from the United States Government, Grant/Contract Number W81XWH-12-1-0468. The government has certain rights in the invention."

And insert:
--This invention was made with government support under grant numbers W81XWH-12-1-0468 and DK078161 awarded by the Department of the Army Medical Research and Materiel Command. The government has certain rights in the invention.--

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*